United States Patent
Ko et al.

(10) Patent No.: US 11,666,619 B2
(45) Date of Patent: Jun. 6, 2023

(54) COMPOSITION FOR TREATING ATOPIC DERMATITIS INCLUDING HERBAL MEDICINE MIXED EXTRACT

(71) Applicant: University—Industry Cooperation Group of Kyung Hee University, Gyeonggi-do (KR)

(72) Inventors: Seong-Gyu Ko, Seoul (KR); Inhwa Choi, Seoul (KR); Younghee Yun, Gyeonggi-do (KR); Se Hyang Hong, Gyeongsangnam-do (KR); Jin Mo Ku, Incheon (KR)

(73) Assignee: K-LAB Corp., Seoul (KR)

( * ) Notice: Subject to any disclaimer, the term of this patent is extended or adjusted under 35 U.S.C. 154(b) by 1085 days.

(21) Appl. No.: 16/329,562

(22) PCT Filed: Sep. 1, 2017

(86) PCT No.: PCT/KR2017/009609
§ 371 (c)(1),
(2) Date: Feb. 28, 2019

(87) PCT Pub. No.: WO2018/044122
PCT Pub. Date: Mar. 8, 2018

(65) Prior Publication Data
US 2019/0336559 A1   Nov. 7, 2019

(30) Foreign Application Priority Data

Sep. 1, 2016   (KR) .......................... 10-2016-0112687

(51) Int. Cl.
| | | |
|---|---|---|
| *A61K 36/756* | (2006.01) | |
| *A61P 29/00* | (2006.01) | |
| *A61K 36/484* | (2006.01) | |
| *A61K 36/489* | (2006.01) | |
| *A61K 36/538* | (2006.01) | |
| *A61K 36/804* | (2006.01) | |
| *A23L 33/105* | (2016.01) | |
| *A61K 8/9789* | (2017.01) | |

(52) U.S. Cl.
CPC .......... *A61K 36/756* (2013.01); *A61K 36/484* (2013.01); *A61K 36/489* (2013.01); *A61K 36/538* (2013.01); *A61K 36/804* (2013.01); *A61P 29/00* (2018.01); *A23L 33/105* (2016.08); *A61K 8/9789* (2017.08); *A61K 2236/333* (2013.01)

(58) Field of Classification Search
None
See application file for complete search history.

(56) References Cited

FOREIGN PATENT DOCUMENTS

| | | |
|---|---|---|
| CN | 103520572 A | 1/2014 |
| KR | 2005/0118820 A | 12/2005 |
| KR | 2013/0077314 A | 7/2013 |
| KR | 2014/0063165 A | 5/2014 |
| KR | 2015/0065250 A | 6/2015 |
| KR | 2016/0019190 A | 2/2016 |
| KR | 101782268 B1 | 9/2017 |
| WO | WO-2011/108907 A2 | 9/2011 |

OTHER PUBLICATIONS

Kim, et al., The Journal of Korean Medicine Opthalmology and Otolaryngology and Dermatology, 27:17. (Year: 2014).*
Sasidharan, et al., Afr. J. Tradit. Complement. Altern. Med., 8:1. (Year: 2011).*
Kim et al "Three Cases of Atopic Dermatitis in Pregnant Woman Successfully Treated with Korean Medicine" Complementary Therapies in Medicine, 2013.
Extended Search Report dated May 4, 2020 for European patent application No. 17 847 047.2.
Kim et al "The Symptoms of Atopic Dermatitis in NC/Nga Mice Were Significantly Relieved by the Water Extract of *Liriope platyphylla*" Laboratory Animal Research vol. 26, pp. 377-384, 2010.
Lee et al "Suppressive Effects of Sojinjiyangtang (SJJY) on Der F-Induced Atopic Dermatitis in NC/Nga Mice" Daejeon University Korean Medical Research Institute vol. 16, pp. 171-190, 2007.
Rousset et al "Shifts in Interleukin-4 and Interferon-γ Production by T Cells of Patients with Elevated Serum IgE Levels and the Modulatory Effects of These Lymphokines on Spontaneous IgE Synthesis" Journal of Allergy and Clinical Immunology vol. 87, pp. 58-69, 1991.
Simon et al "Eosinophils and Atopic Dermatitis" Allergy vol. 59, pp. 561-570, 2004.

* cited by examiner

*Primary Examiner* — Michael Barker
(74) *Attorney, Agent, or Firm* — Cesari & McKenna, LLP

(57) ABSTRACT

Provided are a composition for treating atopic dermatitis including an herbal medicine mixed extract, and more particularly, a pharmaceutical composition, a food composition, a quasi-drug composition, and a cosmetic composition for preventing or treating atopic dermatitis, each composition including a mixed extract of Phellodendri Cortex, Schizonepetae Spica, Sophorae Radix, Glycyrrhizae Radix, Liriopis Tuber, and Radix Rehmanniae Exsiccate or a fraction thereof, and a method of treating atopic dermatitis using the pharmaceutical composition.
The complex herbal medicine extract of the present invention may prevent, ameliorate, and treat atopic dermatitis to a degree similar or superior to those of the known therapeutic agents for atopic dermatitis.

11 Claims, 15 Drawing Sheets

Specification includes a Sequence Listing.

[FIG. 1]
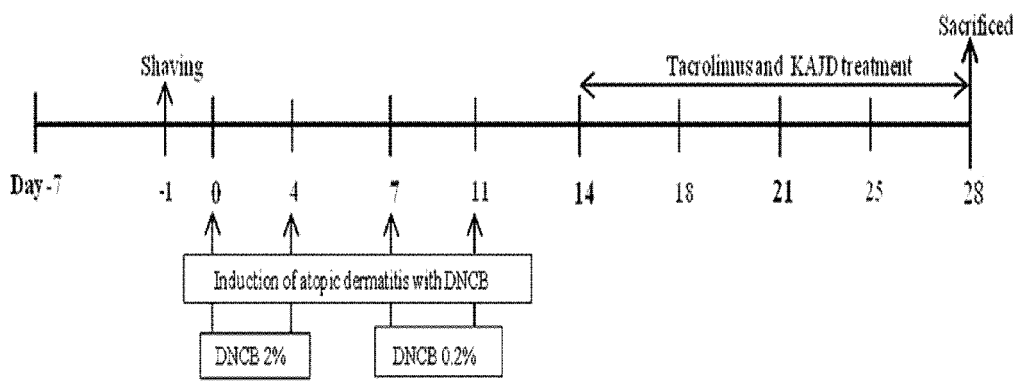
[FIG. 2A]
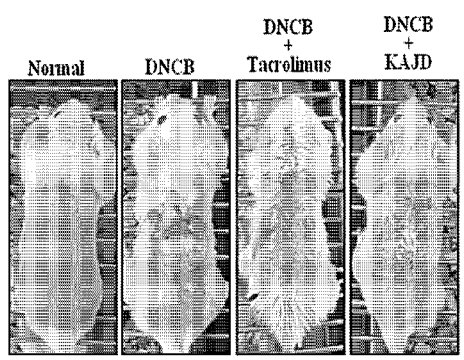
[FIG. 2B]
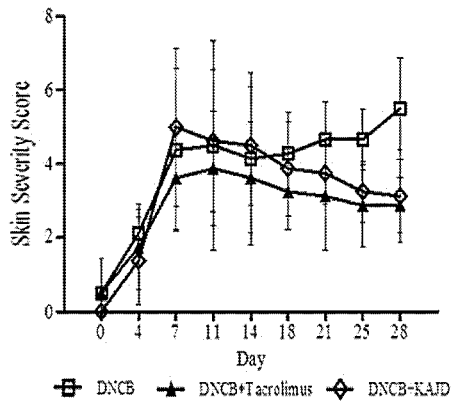
[FIG. 2C]
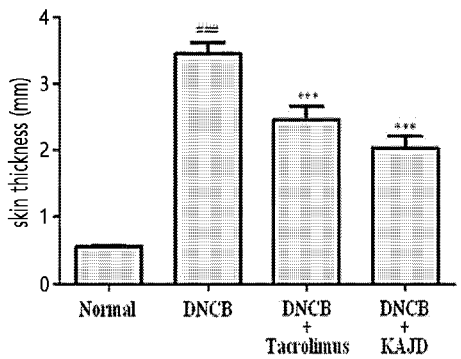
[FIG. 2D]
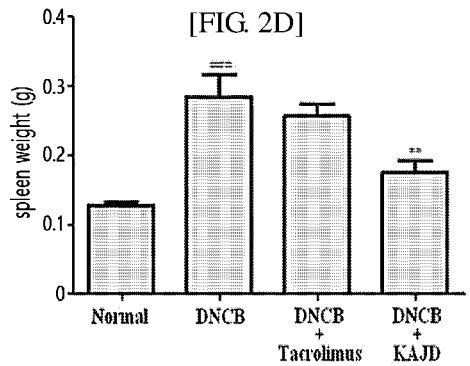

[FIG. 3A]
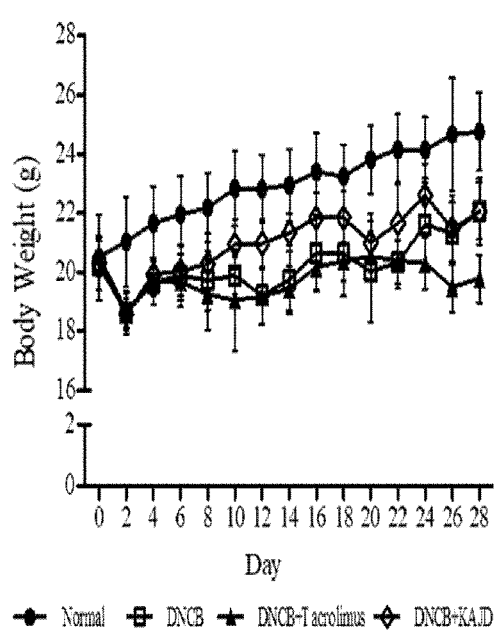
[FIG. 3B]
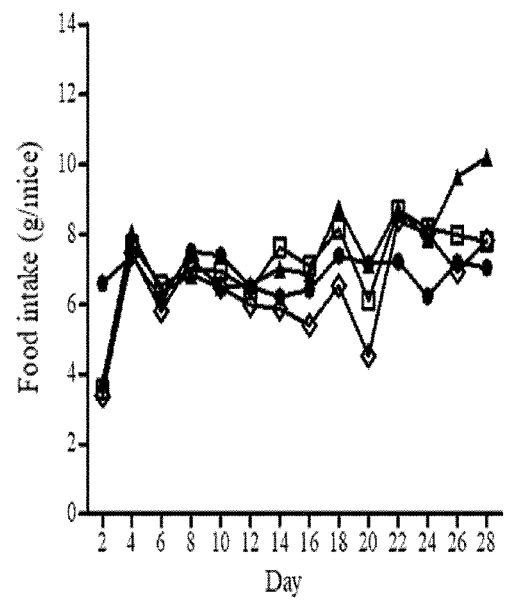

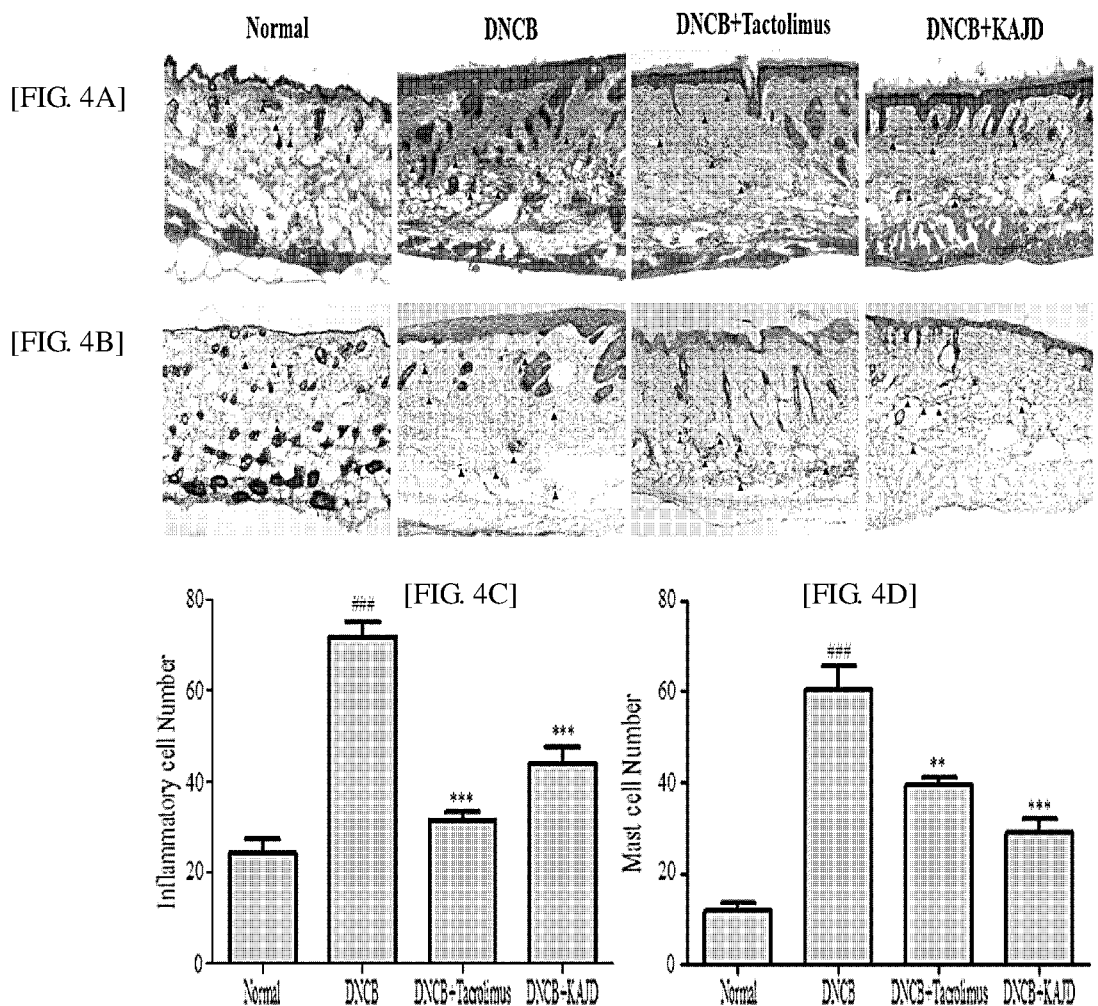

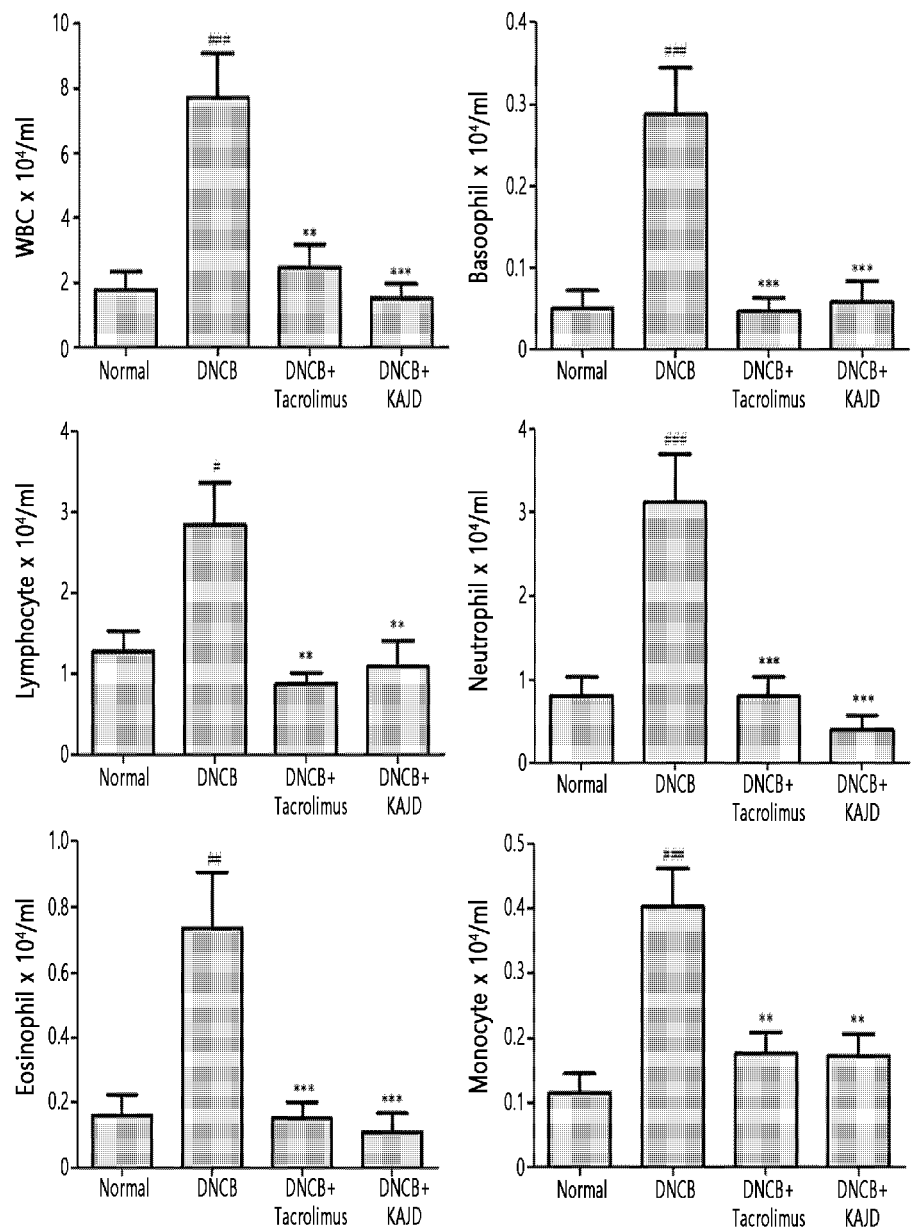
[FIG. 5]

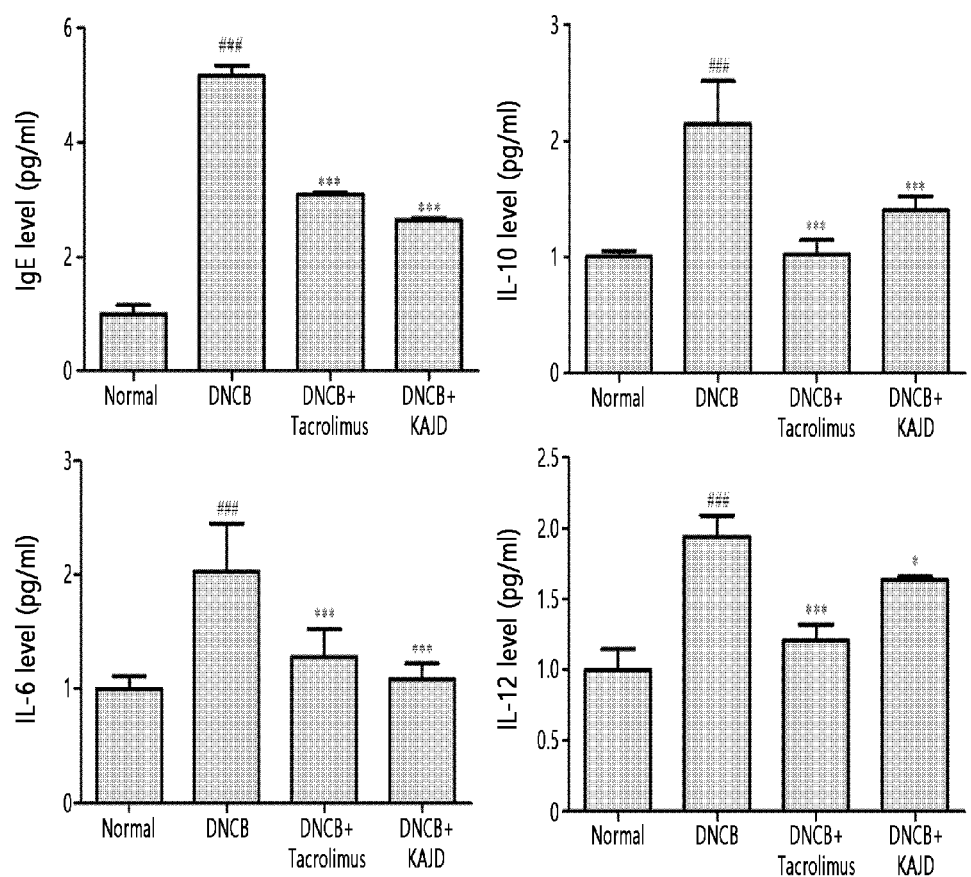
[FIG. 6]

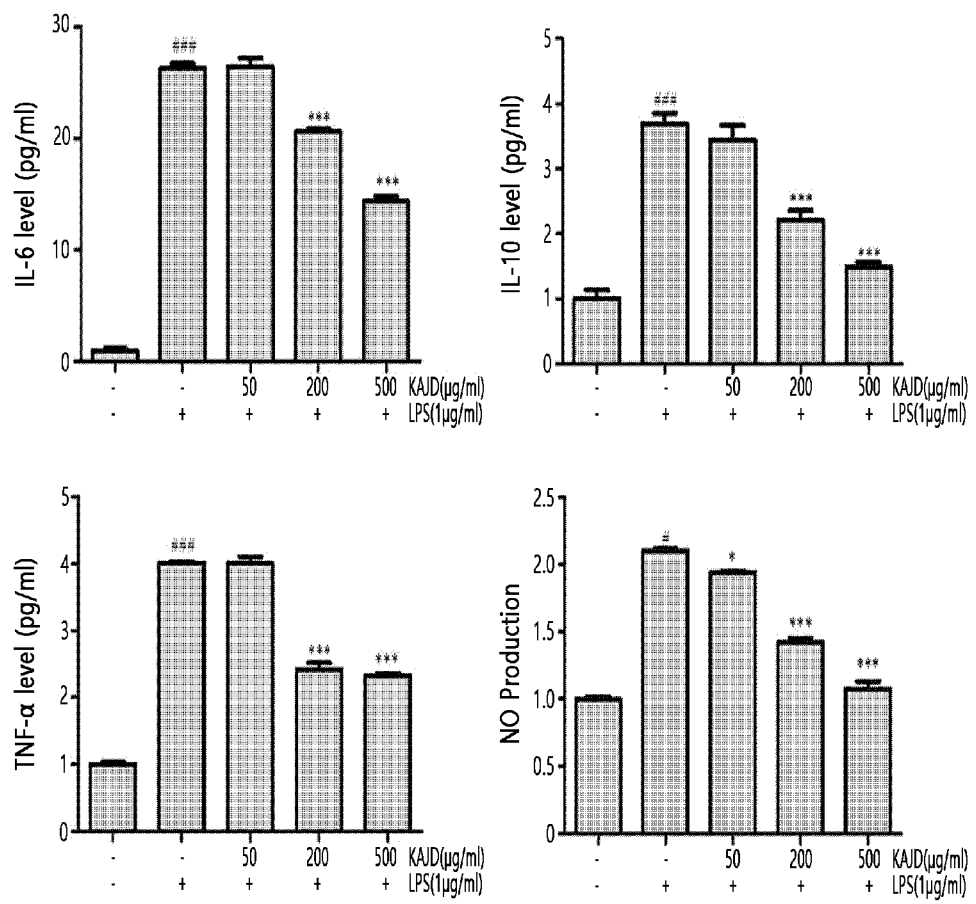
[FIG. 7]

[FIG. 8]
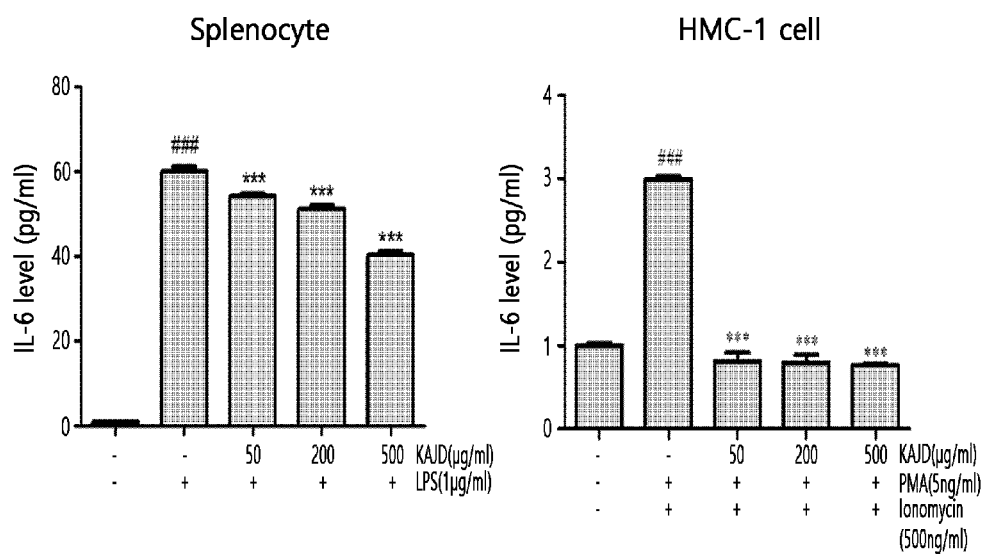

[FIG. 9A]
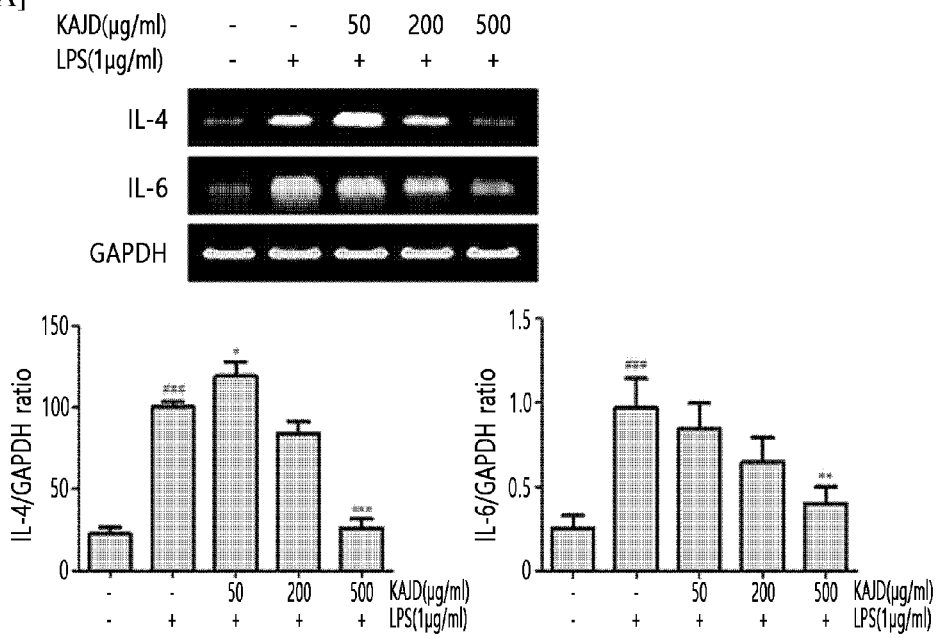
[FIG. 9B]
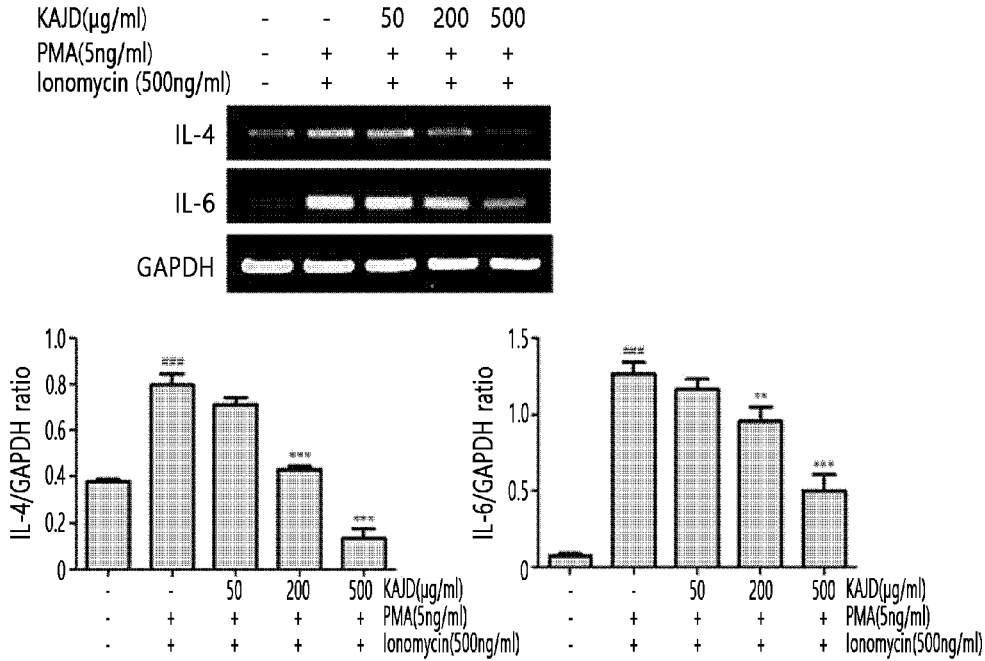

[FIG. 10A]
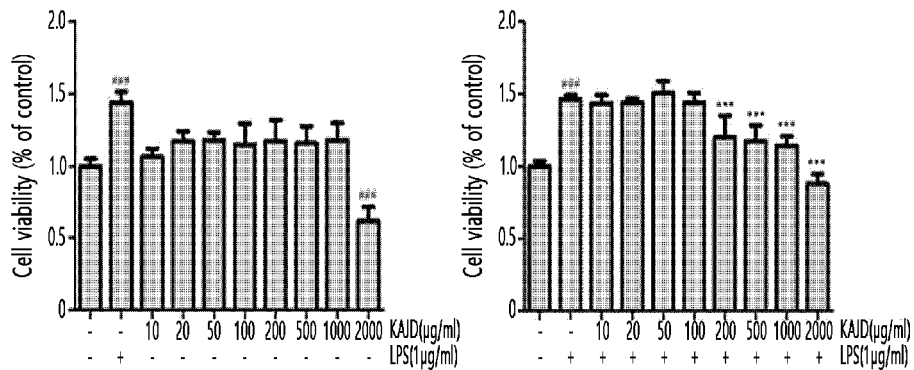
[FIG. 10B]
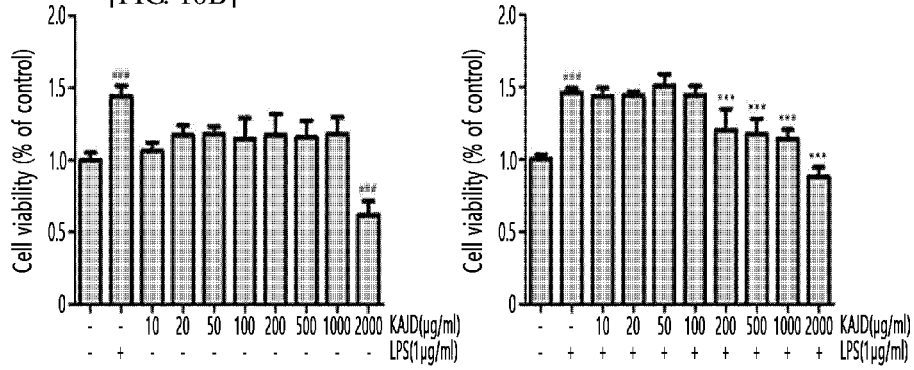
[FIG. 10C]
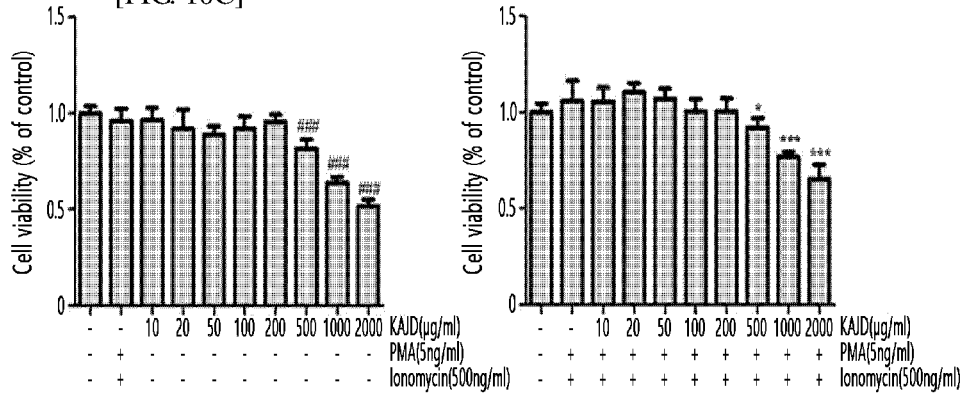

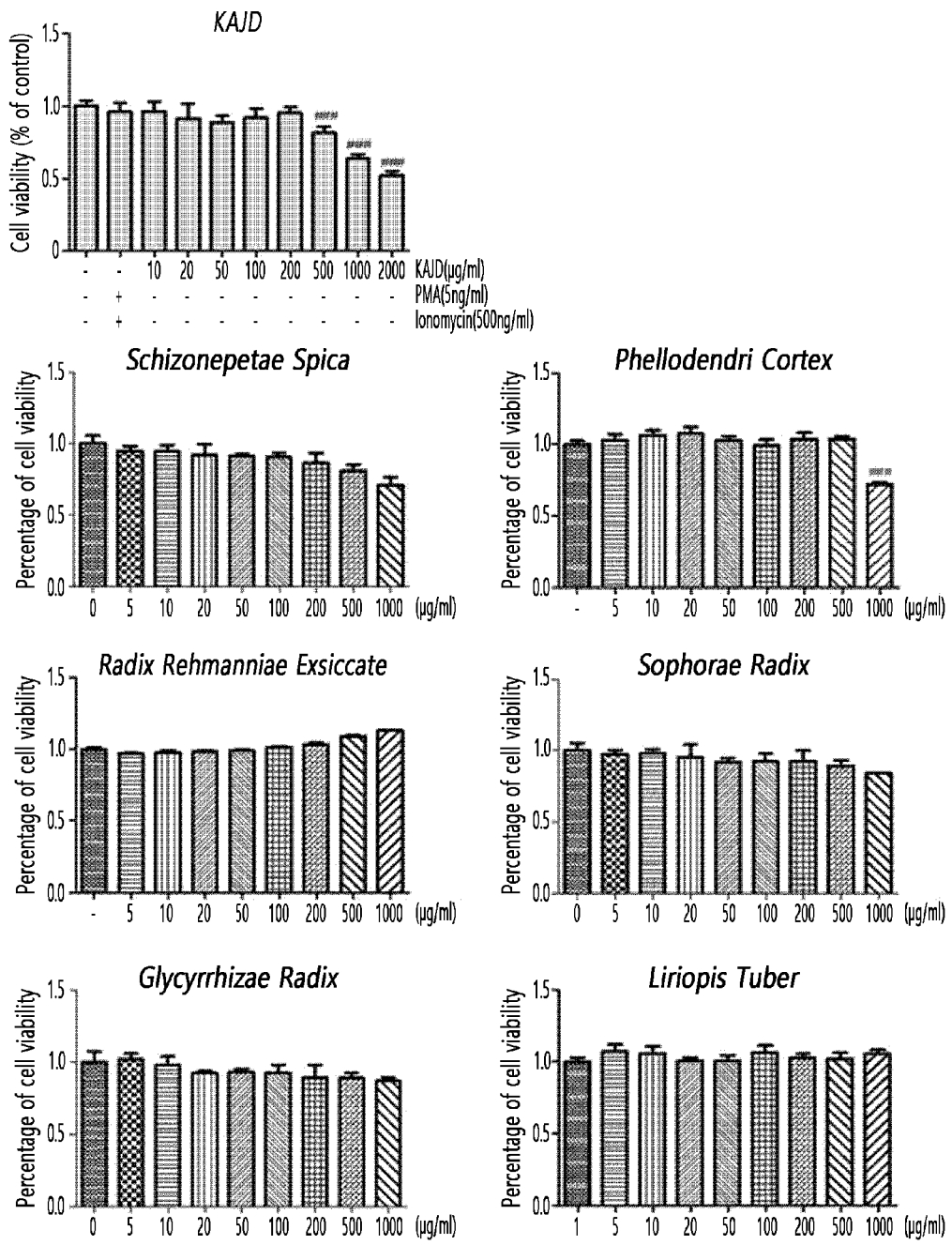
[FIG. 11A]

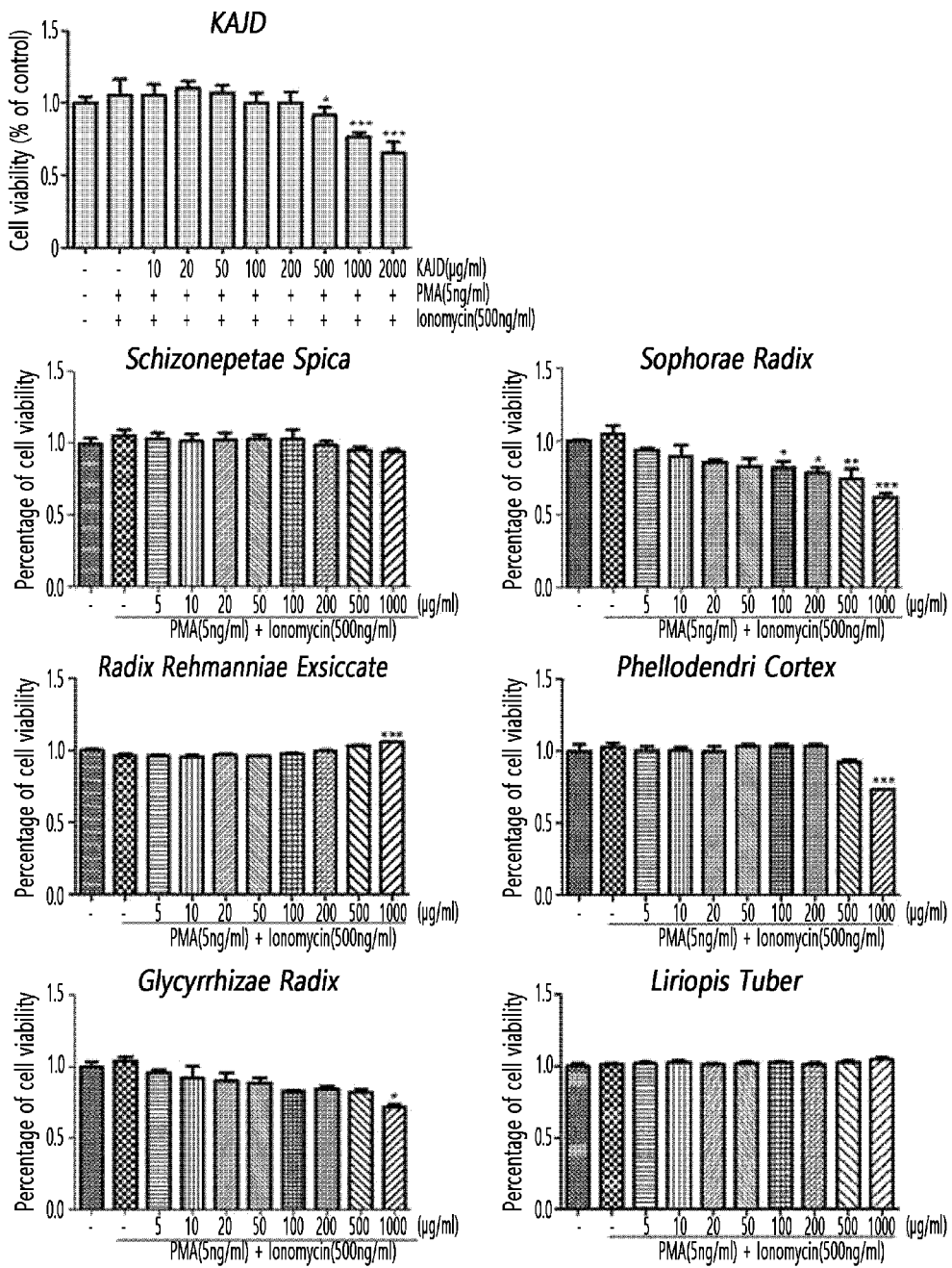
[FIG. 11B]

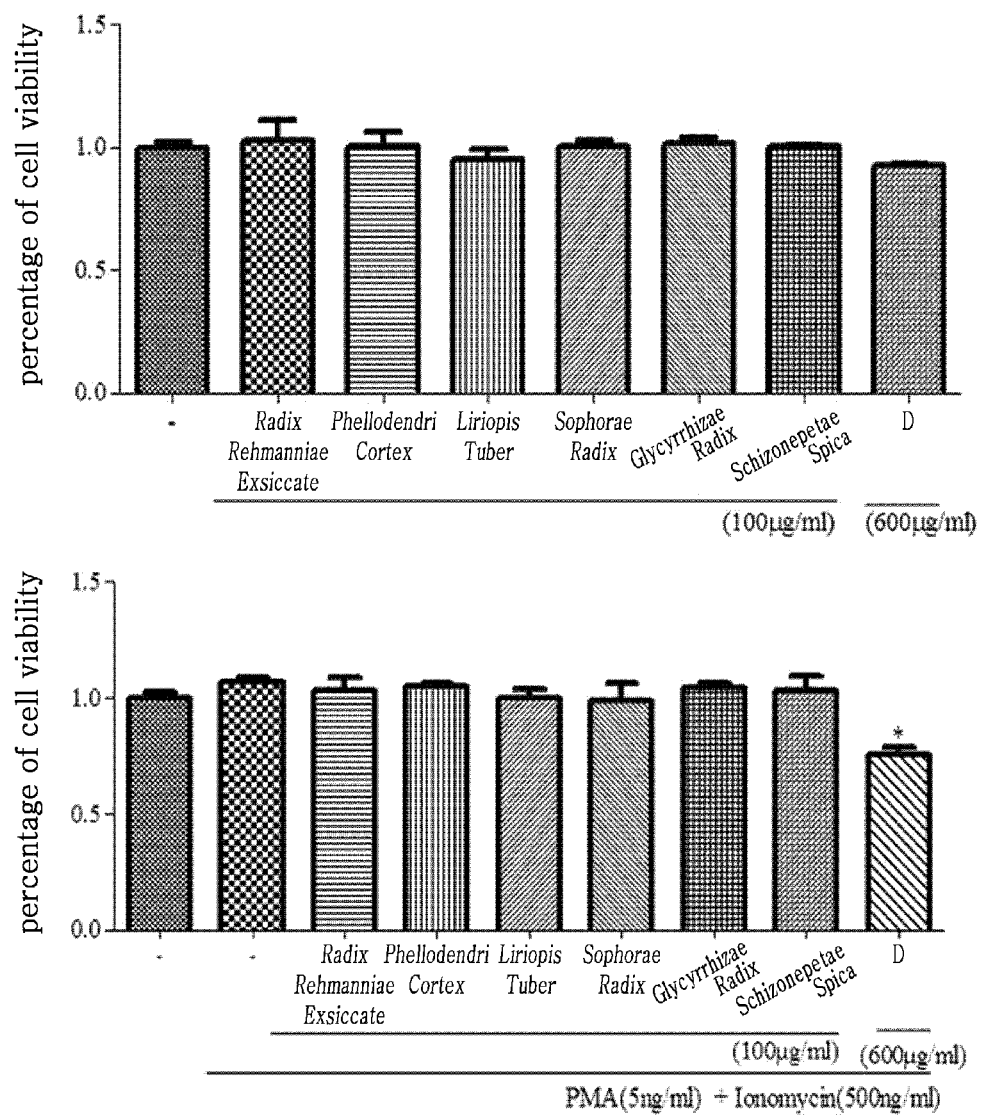
[FIG. 12]

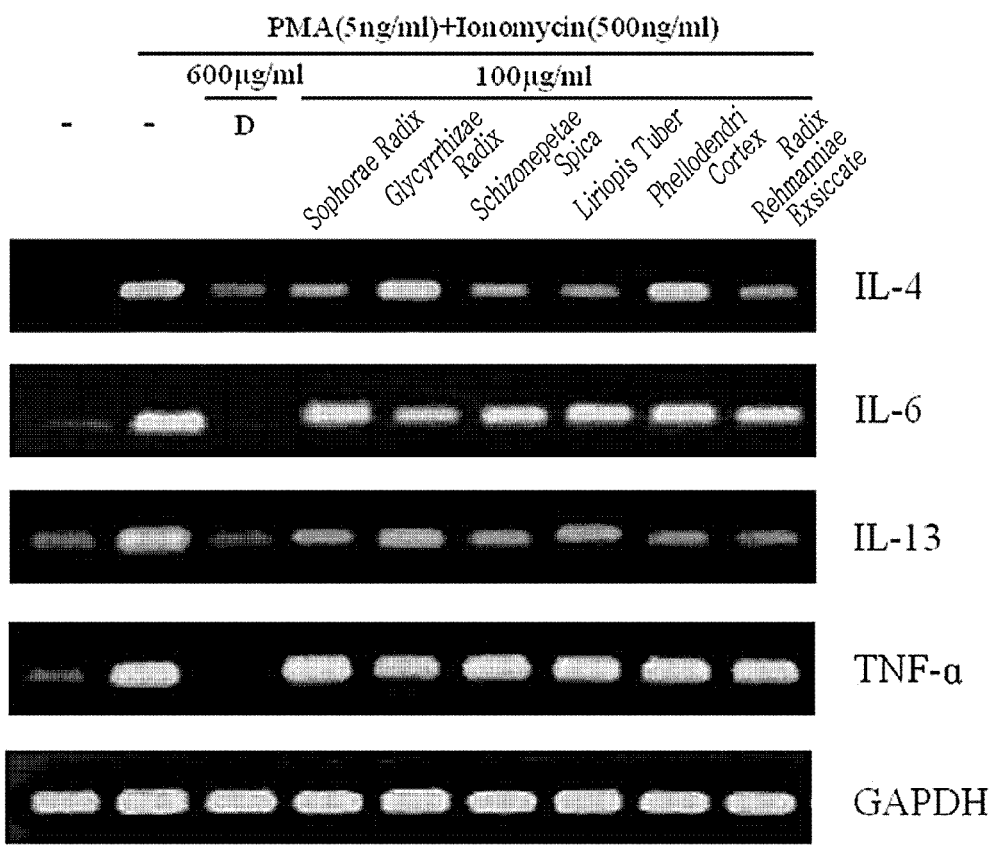
[FIG. 13]

[FIG. 14]
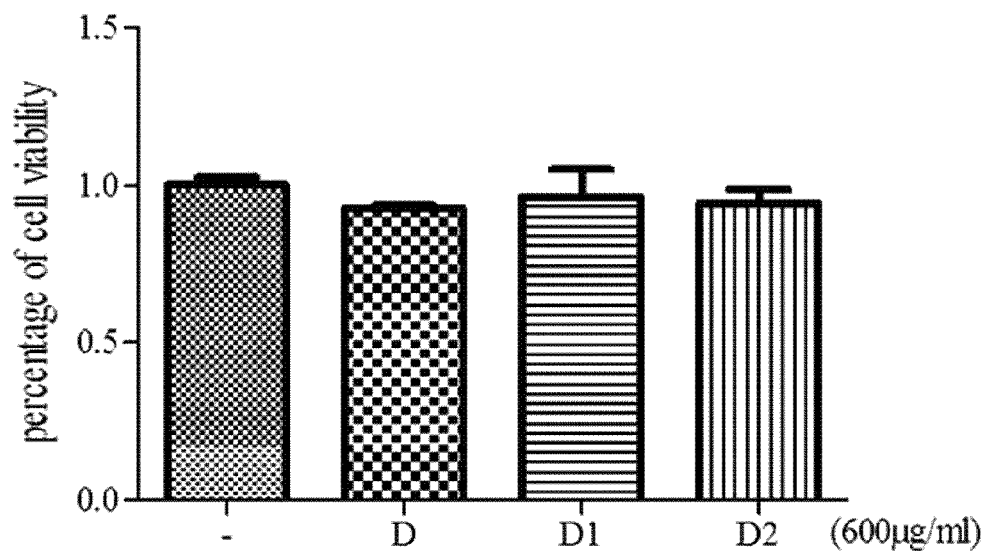
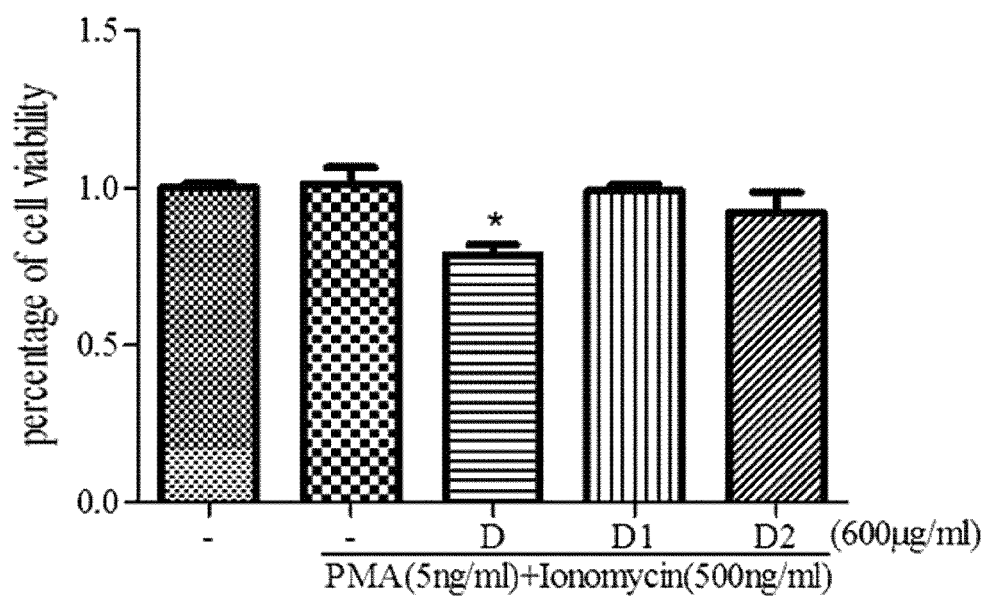

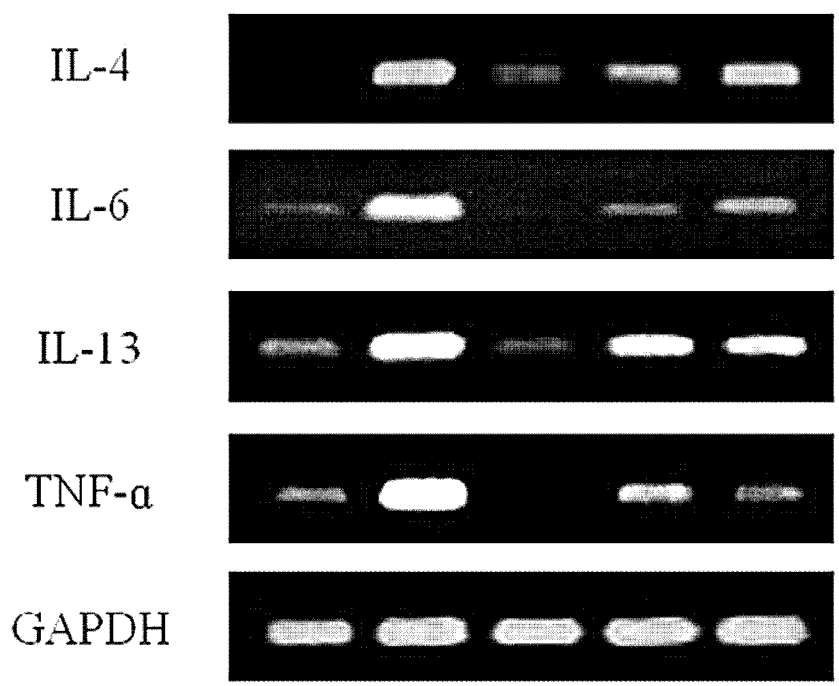

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: IL-4 forward primer

<400> SEQUENCE: 1

```
tcggcatttt gaacgaggtc                                              20

<210> SEQ ID NO 2
<211> LENGTH: 20
<212> TYPE: DNA
<213> ORGANISM: Artificial Sequence
<220> FEATURE:
<223> OTHER INFORMATION: IL-4 reverse primer

<400> SEQUENCE: 2
gaaaagcccg aaagagtctc                                              20

<210> SEQ ID NO 3
<211> LENGTH: 22
<212> TYPE: DNA
<213> ORGANISM: Artificial Sequence
<220> FEATURE:
<223> OTHER INFORMATION: IL-6 forward primer

<400> SEQUENCE: 3
caagagactt ccatccagtt gc                                           22

<210> SEQ ID NO 4
<211> LENGTH: 21
<212> TYPE: DNA
<213> ORGANISM: Artificial Sequence
<220> FEATURE:
<223> OTHER INFORMATION: IL-6 reverse primer

<400> SEQUENCE: 4
ttgccgagtt ctcaaagtga c                                            21

<210> SEQ ID NO 5
<211> LENGTH: 20
<212> TYPE: DNA
<213> ORGANISM: Artificial Sequence
<220> FEATURE:
<223> OTHER INFORMATION: COX-2 forward primer

<400> SEQUENCE: 5
aagacttgcc aggctgaact                                              20

<210> SEQ ID NO 6
<211> LENGTH: 21
<212> TYPE: DNA
<213> ORGANISM: Artificial Sequence
<220> FEATURE:
<223> OTHER INFORMATION: COX-2 reverse primer

<400> SEQUENCE: 6
cttctgcagt cccaggttca a                                            21

<210> SEQ ID NO 7
<211> LENGTH: 27
<212> TYPE: DNA
<213> ORGANISM: Artificial Sequence
<220> FEATURE:
<223> OTHER INFORMATION: iNOS forward primer

<400> SEQUENCE: 7
aatggcaaca tcaggtcggc catcact                                      27

<210> SEQ ID NO 8
<211> LENGTH: 27
<212> TYPE: DNA
```

```
<213> ORGANISM: Artificial Sequence
<220> FEATURE:
<223> OTHER INFORMATION: iNOS reverse primer

<400> SEQUENCE: 8
gctgtgtgtc acagaagtct cgaactc                                         27

<210> SEQ ID NO 9
<211> LENGTH: 21
<212> TYPE: DNA
<213> ORGANISM: Artificial Sequence
<220> FEATURE:
<223> OTHER INFORMATION: TNF-a forward primer

<400> SEQUENCE: 9
atgagcacag aaagcatgat c                                               21

<210> SEQ ID NO 10
<211> LENGTH: 21
<212> TYPE: DNA
<213> ORGANISM: Artificial Sequence
<220> FEATURE:
<223> OTHER INFORMATION: TNF-a reverse primer

<400> SEQUENCE: 10
tacaggcttg tcactggaat t                                               21

<210> SEQ ID NO 11
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 11
gaggggccat ccacagtctt c                                               21

<210> SEQ ID NO 12
<211> LENGTH: 21
<212> TYPE: DNA
<213> ORGANISM: Artificial Sequence
<220> FEATURE:
<223> OTHER INFORMATION: GAPDH reverse primer

<400> SEQUENCE: 12
catcaccatc ttccaggagc g                                               21

<210> SEQ ID NO 13
<211> LENGTH: 20
<212> TYPE: DNA
<213> ORGANISM: Artificial Sequence
<220> FEATURE:
<223> OTHER INFORMATION: IL-4 forward primer

<400> SEQUENCE: 13
tgcctccaag aacacaactg                                                 20

<210> SEQ ID NO 14
<211> LENGTH: 20
<212> TYPE: DNA
<213> ORGANISM: Artificial Sequence
<220> FEATURE:
<223> OTHER INFORMATION: IL-4 reverse primer

<400> SEQUENCE: 14
ctctggttgg cttccttcac                                                 20
```

```
<210> SEQ ID NO 15
<211> LENGTH: 21
<212> TYPE: DNA
<213> ORGANISM: Artificial Sequence
<220> FEATURE:
<223> OTHER INFORMATION: IL-6 forward primer

<400> SEQUENCE: 15
aaccttccaa agatggctag g                                              21

<210> SEQ ID NO 16
<211> LENGTH: 21
<212> TYPE: DNA
<213> ORGANISM: Artificial Sequence
<220> FEATURE:
<223> OTHER INFORMATION: IL-6 reverse primer

<400> SEQUENCE: 16
caggaactgg atcaggactt t                                              21

<210> SEQ ID NO 17
<211> LENGTH: 20
<212> TYPE: DNA
<213> ORGANISM: Artificial Sequence
<220> FEATURE:
<223> OTHER INFORMATION: IL-13 forward primer

<400> SEQUENCE: 17
ggtcaacatc acccagaacc                                                20

<210> SEQ ID NO 18
<211> LENGTH: 20
<212> TYPE: DNA
<213> ORGANISM: Artificial Sequence
<220> FEATURE:
<223> OTHER INFORMATION: IL-13 reverse primer

<400> SEQUENCE: 18
tttacaaact gggccacctc                                                20

<210> SEQ ID NO 19
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 19
cgtcttcacc accatggaga                                                20

<210> SEQ ID NO 20
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 20
cggccatcac gccacagttt                                                20
```

COMPOSITION FOR TREATING ATOPIC DERMATITIS INCLUDING HERBAL MEDICINE MIXED EXTRACT

CROSS-REFERENCE TO RELATED APPLICATIONS

This application is the National Stage of International Application No. PCT/KR2017/009609, filed Sep. 1, 2017, which claims the benefit of Korean Application No. 10-2016-0112687, filed Sep. 1, 2016. The contents of both applications are hereby incorporated by reference in their entirety.

TECHNICAL FIELD

The present invention relates to a composition for treating atopic dermatitis including an herbal medicine mixed extract, and more particularly, a pharmaceutical composition, a food composition, a quasi-drug composition, and a cosmetic composition for preventing or treating atopic dermatitis, each composition including a mixed extract of Phellodendri Cortex, Schizonepetae Spica, Sophorae Radix, Glycyrrhizae Radix, Liriopis Tuber, and Radix Rehmanniae Exsiccate or a fraction thereof, and a method of treating atopic dermatitis using the pharmaceutical composition.

BACKGROUND ART

Atopic dermatitis (AD) is a chronic inflammatory skin disease that commonly occurs, and occasionally, develops allergic disorders such as food allergy, asthma, or rhinitis. AD is characterized by increasing the number of eosinophils, serum IgE levels, and proinflammatory cytokines including TNF-α, chemokines, etc. (Simon D. et al., Allergy, 2004, 59, 561-570; Rousset F. et al., J Allergy Clin Immunol., 1991, 87, 58-69). IgE induces mast cell activation, leading to release of inflammatory mediators including histamine precursor, chemokines, and cytokines from mast cells. These cytokines promote Th2 subtype T-cell responses which are observed in skin lesions of acute AD, and immune responses are regulated by a combination of Th2 and Th1 responses during the chronic phase of AD.

Topical corticosteroids are the standard therapies for acute AD, but they are reported to have atrophogenic side effects (Lubach D. et al., Dermatologica, 1989, 179, 67-72). It is necessary to develop anti-inflammatory factors without steroids which are safe even if used for a long period of time. In this regard, tacrolimus, which is a topical immunosuppressant, is currently being used to treat AD. Tacrolimus has been used in the form of a topical ointment because it effectively penetrates into the skin because of its relatively small molecular size (Akhavan A. et al., Semin Cutan Med Surg., 2008, 27, 151-155). Tacrolimus does not cause collagen synthesis or scleroderma, which is one of the side effects of corticosteroids, and can be safely used on thin and delicate areas, such as the face or neck. However, long-term use of tacrolimus was reported to counter its effects and to cause side effects, and thus development of a new drug for treating AD is required.

Accordingly, development of therapeutic agents for atopic dermatitis using natural products is actively underway, and a composition for improving atopic dermatitis including a ginsenoside Rd-enhanced fermented *ginseng* or red *ginseng* extract (Korean Patent Publication No. 2016-0019190), cosmetics for atopic skin including *Eucommia ulmoides* Oliver and *Polygala tenuifolia* extracts (Korean Patent Publication No. 2015-0065250), a composition for improving atopic dermatitis including a millet extract (Korean Patent Publication No. 2014-0063165), etc. have been developed.

Meanwhile, Phellodendri Cortex, Schizonepetae Spica, Sophorae Radix, Glycyrrhizae Radix, Liriopis Tuber, and Radix Rehmanniae Exsiccate are medicinal products used in Oriental medicine, and are known to have therapeutic effects on menopause, cirrhosis, digestive action, antibacterial action, metrorrhagia, menstrual disorder, dysentery, leukorrhea, pruritus *genitalium*, etc. However, there have been no reports about use of combinations thereof as drugs and effects of combinations thereof on atopic dermatitis.

DISCLOSURE

Technical Problem

The present inventors have made intensive efforts to develop therapeutic agents for atopic dermatitis using natural products, and as a result, they found that a mixed extract of Phellodendri Cortex, Schizonepetae Spica, Sophorae Radix, Glycyrrhizae Radix, Liriopis Tuber, and Radix Rehmanniae Exsiccate suppresses immune responses to treat atopic dermatitis, thereby completing the present invention.

Technical Solution

An object of the present invention is to provide a pharmaceutical composition for preventing or treating atopic dermatitis, the pharmaceutical composition including a mixed extract of Phellodendri Cortex, Schizonepetae Spica, Sophorae Radix, Glycyrrhizae Radix, Liriopis Tuber, and Radix Rehmanniae Exsiccate or a fraction thereof.

Another object of the present invention is to provide a method of treating atopic dermatitis, the method including the step of administering the pharmaceutical composition to a subject suspected of having atopic dermatitis, excluding humans.

Still another object of the present invention is to provide a food composition for ameliorating atopic dermatitis, the food composition including a mixed extract of Phellodendri Cortex, Schizonepetae Spica, Sophorae Radix, Glycyrrhizae Radix, Liriopis Tuber, and Radix Rehmanniae Exsiccate or a fraction thereof.

Still another object of the present invention is to provide a quasi-drug composition for preventing or ameliorating atopic dermatitis, the quasi-drug composition including a mixed extract of Phellodendri Cortex, Schizonepetae Spica, Sophorae Radix, Glycyrrhizae Radix, Liriopis Tuber, and Radix Rehmanniae Exsiccate or a fraction thereof.

Still another object of the present invention is to provide a cosmetic composition for preventing or ameliorating atopic dermatitis, the quasi-drug composition including a mixed extract of Phellodendri Cortex, Schizonepetae Spica, Sophorae Radix, Glycyrrhizae Radix, Liriopis Tuber, and Radix Rehmanniae Exsiccate or a fraction thereof.

Advantageous Effects

A complex herbal medicine extract of the present invention may prevent, ameliorate, and treat atopic dermatitis to a degree similar or superior to those of the known therapeutic agents for atopic dermatitis.

DESCRIPTION OF DRAWINGS

FIG. 1 is a schematic illustration of an experiment to examine therapeutic effects of KAJD (a mixed extract of Phellodendri Cortex, Schizonepetae Spica, Sophorae Radix, Glycyrrhizae Radix, Liriopis Tuber, and Radix Rehmanniae Exsiccate) on atopic dermatitis. Atopic dermatitis was induced by DNCB, and then KAJD was orally administered.

FIGS. 2A-2D show effects of KAJD on atopic dermatitis (AD). FIG. 2A is an image of the dorsal skin observed after treatment with KAJD (n=8). FIG. 2B is a graph showing severity score of AD-induced skin lesions (individual scores that evaluated each symptom of erythema/bleeding, edema, exfoliation/dryness, excoriation/erosion were added and expressed as a total score). FIG. 2C shows thickness of the dorsal skin after treatment with KAJD or tacrolimus. FIG. 2D is a graph showing the spleen weight. ### represents $P<0.001$ in comparison to a normal control group, and  and * represent $P<0.01$ and $P<0.001$ in comparison to a DNCB-treated group, respectively.

FIGS. 3A and 3B are a graph showing changes in the body weight (3A) and food intake (3B) during treatment with KAJD. The results were expressed as mean±SEM (n=8).

FIGS. 4A-4D show effects of KAJD on skin infiltration of proinflammatory cells and mast cells. FIG. 4A shows hematoxylin and eosin (H&E) staining images of the dorsal skin sections. FIG. 4B shows toluidine blue staining images of the dorsal skin sections. Inflammatory cells in each image were indicated by purple dots. FIG. 4C is a graph showing the number of stained inflammatory cells. FIG. 4D is a graph showing the number of stained mast cells. The results were expressed as mean±SEM. ### represents $P<0.001$ in comparison to a normal control group, and  and * represent $P<0.01$ and $P<0.001$ in comparison to a DNCB-treated group, respectively.

FIG. 5 shows effects of KAJD on blood components. Each graph shows the number of white blood cell (WBCs), lymphocytes, monocytes, eosinophils, basophils, or neutrophils. The results were expressed as mean±SEM. # and ### represent $P<0.05$ and $P<0.001$ in comparison to a normal control group, respectively, and  and * represent $P<0.01$ and $P<0.001$ in comparison to a DNCB-treated group, respectively.

FIG. 6 shows effects of KAJD on expression levels of serum IgE and cytokines. IgE, IL-6, IL-10, and IL-12 levels in the blood were measured by ELISA assay. ### represents $P<0.001$ in comparison to a normal control group, and * and *** represent $P<0.05$ and $P<0.001$ in comparison to a DNCB-treated group, respectively.

FIG. 7 shows effects of KAJD on NO (nitric oxide) production and proinflammatory cytokine expression in RAW264.7 cells. RAW264.7 cells were not treated or treated with LPS (1 µg/mL) for 1 hour, and then treated with 50 g/mL, 200 µg/mL, or 500 µg/mL of KAJD for an additional 24 hours. NO amount in the cell culture was measured using a Griess reagent, and IL-6, IL-10, and TNF-α levels were measured by ELISA assay. The results were expressed as mean±SEM. # represents $P<0.05$ in comparison to a normal control group, and * and *** represent $P<0.05$ and $P<0.001$ in comparison to a DNCB-treated group, respectively.

FIG. 8 shows effects of KAJD on IL-6 expression in splenocytes and HMC-1 cells. Splenocytes were not treated or treated with LPS (1 µg/mL) for 1 hour; and HMC-1 cells were not treated or treated with PMA (5 ng/mL) and ionomycin (500 ng/mL) for 1 hour, and then each treated with 50 µg/mL, 200 µg/mL, or 500 µg/mL of KAJD for an additional 24 hours. IL-6 levels were measured by ELISA assay. The results were expressed as mean±SEM. ### represents $P<0.001$ in comparison to a normal control group, and  and * represent $P<0.01$ and $P<0.001$ in comparison to a DNCB-treated group, respectively.

FIGS. 9A and 9B show effects of KAJD on mRNA expressions of proinflammatory cytokines in splenocytes (9A) or HMC-1 cells (9B). Splenocytes were not treated or treated with LPS (1 µg/mL) for 1 hour; and HMC-1 cells were not treated or treated with PMA (5 ng/mL) and ionomycin (500 ng/mL) for 1 hour, and then each treated with 50 µg/mL, 200 µg/mL, or 500 µg/mL of KAJD for an additional 24 hours. mRNA levels of IL-4 or IL-6 were measured by RT-PCR. The results were expressed as mean±SEM. ### represents $P<0.001$ in comparison to a normal control group, and  and * represent $P<0.01$ and $P<0.001$ in comparison to a DNCB-treated group, respectively.

FIGS. 10A-10C show effects of KAJD on viability of inflammation-related cells. FIGS. 10A, 10B, and 10C show results for RAW264.7 cells, splenocytes, and HMC-1 cells, respectively. RAW264.7 cells and splenocytes were treated with LPS (1 µg/mL), and HMC-1 cells were treated with PMA (5 ng/mL) and ionomycin (500 ng/mL) for 1 hour, and then each treated with various concentrations of KAJD for an additional 24 hours. After completion of the treatment, cell viability was measured by WST assay. The results were expressed as mean±SEM. In FIG. 10A, ### represents $P<0.001$ in comparison to a normal control group, and * represents $P<0.001$ in comparison to an inflammation control group. In FIG. 10B, ## represents $P<0.01$ in comparison to a normal control group, and  represents $P<0.01$ in comparison to an inflammation control group. In FIG. 10C, ### represents $P<0.001$ in comparison to a normal control group, and * and *** represent $P<0.05$ and $P<0.001$ in comparison to an inflammation control group, respectively.

FIGS. 11A and 11B show the results of comparing inflammatory cell viability-reducing effects between a mixed herbal medicine extract (KAJD; D) and single herbal medicine extracts. FIG. 11A shows the result for non-activated HMC-1 cells, and FIG. 11B shows the result for HMC-1 cells activated at an inflammatory state by PMA (5 ng/mL) and ionomycin (500 ng/mL). HMC-1 cell viability was measured by MTT assay. The results were expressed as mean±SEM. ### represents $P<0.001$ in comparison to a normal control group, and *, , and * represent $P<0.05$, $P<0.01$, and $P<0.001$ in comparison to an inflammation control group, respectively.

FIG. 12 shows the results of comparing inflammatory cell viability-reducing effects between a mixed herbal medicine extract (KAJD; D) and single herbal medicine extracts. HMC-1 cells were treated with a single extract of Phellodendri Cortex, Liriopis Tuber, Schizonepetae Spica, Radix Rehmanniae Exsiccate, Sophorae Radix, or Glycyrrhizae Radix (100 µg/mL), or KAJD (D, 500 µg/mL) for 24 hours. HMC-1 cell viability was measured by MTT assay. The results were expressed as mean±SEM, and * represents $P<0.05$ in comparison to a negative control group.

FIG. 13 shows the results of comparing proinflammatory cytokine expression-reducing effects between a mixed herbal medicine extract (KAJD; D) and single herbal medicine extracts. A single extract of Phellodendri Cortex, Liriopis Tuber, Schizonepetae Spica, Radix Rehmanniae Exsiccate, Sophorae Radix, or Glycyrrhizae Radix (100 µg/mL), or KAJD (D, 500 µg/mL) was treated for 24 hours. mRNA expression levels of proinflammatory cytokines (IL-4, IL-6, IL-13, and TNF-α) in activated HMC-1 mast cells were measured by PCR, and in this regard, GAPDH was used as a loading control.

FIG. 14 shows inflammatory cell viability-reducing effects according to a mixing ratio of herbal medicines constituting KAJD. In graphs, D, D1, and D2 represent mixed herbal medicine extracts including Phellodendri Cortex, Liriopis Tuber, Schizonepetae Spica, Radix Rehmanniae Exsiccate, Sophorae Radix, and Glycyrrhizae Radix at weight ratios of 1:1:1:1:1:1, 1:1:1:1:2:1, and 1:1:1:1:1:2, respectively. HMC-1 cell viability was measured by MTT assay. The results were expressed as mean±SEM, and * represents $P<0.05$ in comparison to a negative control group.

FIG. 15 shows proinflammatory cytokine expression-reducing effects according to a mixing ratio of herbal medicines constituting KAJD. In graphs, D, D1, and D2 represent mixed herbal medicine extracts including Phellodendri Cortex, Liriopis Tuber, Schizonepetae Spica, Radix Rehmanniae Exsiccate, Sophorae Radix, and Glycyrrhizae Radix at weight ratios of 1:1:1:1:1:1, 1:1:1:1:2:1, and 1:1:1:1:1:2, respectively. mRNA expressions of proinflammatory cytokines (IL-4, IL-6, IL-13, and TNF-α) were examined in activated HMC-1 mast cells, and in this regard, GAPDH was used as a loading control.

BEST MODE

To achieve the above objects, an aspect provides a pharmaceutical composition for preventing or treating atopic dermatitis, the pharmaceutical composition including a mixed extract of Phellodendri Cortex, Schizonepetae Spica, Sophorae Radix, Glycyrrhizae Radix, Liriopis Tuber, and Radix Rehmanniae Exsiccate or a fraction thereof.

In the present invention, it was found that the mixed extract of Phellodendri Cortex, Schizonepetae Spica, Sophorae Radix, Glycyrrhizae Radix, Liriopis Tuber, and Radix Rehmanniae Exsiccate may effectively alleviate symptoms of atopic dermatitis, and therefore, the extract may be used as a therapeutic agent for atopic dermatitis. The therapeutic effects of the combination of Phellodendri Cortex, Schizonepetae Spica, Sophorae Radix, Glycyrrhizae Radix, Liriopis Tuber, and Radix Rehmanniae Exsiccate on atopic dermatitis have not been previously known, and were demonstrated for the first time by the present inventors.

As used herein, the term "Phellodendri Cortex" refers to a medicinal product obtained by drying the bark of *Phellodendron amurense*. Phellodendri Cortex is the name of an herbal medicine, and its scientific name is *Phellodendron wilsonii*. Phellodendri Cortex is known to have a bitter taste and a cold property, and as being used in the kidney meridian, bladder meridian, large intestine meridian, pericardium meridian, etc.

As used herein, the term "Schizonepetae Spica" refers to a product obtained by drying the whole plant of Schizonepetae Spica, which is a plant belonging to the family Lamiaceae. Schizonepetae Spica is the name of an herbal medicine, and its scientific name is *Schizonepeta tenuifolia*. Schizonepeta Spica is known to have a bitter taste and a warm property, to act on the lung meridian, liver meridian, etc., and to exhibit digestive action, antimicrobial action, etc.

As used herein, the term "Sophorae Radix" refers to a root resulting from peeling off the periderm of Sophorae Radix. Sophorae Radix is the name of an herbal medicine, and its scientific name is *Sophora flavescens*. Sophorae Radix has a peculiar persistent smell, and has very bitter and cold medicinal properties. Due to its property of clearing the damp-heat of the lower energizer, Sophorae Radix is known to be used for dysentery, leukorrhea, pruritus *genitalium*, itchy skin, etc., and also to be used for pains caused by cystoschisis.

As used herein, the term "Glycyrrhizae Radix" refers to a product obtained by drying the root or stem of Glycyrrhizae Radix. Glycyrrhizae Radix is the name of an herbal medicine, and its scientific name is *Glycyrrhiza glabra*. Sophorae Radix is characterized by having a peculiar smell and a sweet taste. It is known that Glycyrrhizae Radix harmonizes the toxicity of all drugs to make them effective, controls chill and fever and pathogenic factors of internal organs, replenishes all blood vessels, and strengthens muscles and bones.

As used herein, the term "Radix Rehmanniae Exsiccate" refers to a product obtained by drying the rhizome of *Rehmannia glutinosa*, which is a plant belonging to the family Scrophulariaceae. Radix Rehmanniae Exsiccate or Rehmanniae Radix is the name of an herbal medicine, and its scientific name is Rehmanniae Exsiccat or *Rehmannia* adj *glutinosa*. Radix Rehmanniae Exsiccate is characterized by having a sweet taste and a cold property. It is known that Radix Rehmanniae Exsiccate exhibits diuretic and blood sugar-lowering effects and is used for metrorrhagia, menstrual disorder, constipation, general weakness, etc.

In the present invention, the mixed extract of Phellodendri Cortex, Schizonepetae Spica, Sophorae Radix, Glycyrrhizae Radix, Liriopis Tuber, and Radix Rehmanniae Exsiccate may be used interchangeably with "KAJD" or "KHU-ATO-JIN-D". The mixed extract may be an extract of a mixture of Phellodendri Cortex, Schizonepetae Spica, Sophorae Radix, Glycyrrhizae Radix, Liriopis Tuber, and Radix Rehmanniae Exsiccate, and may also be a mixture of Phellodendri Cortex, Schizonepetae Spica, Sophorae Radix, Glycyrrhizae Radix, Liriopis Tuber, and Radix Rehmanniae Exsiccate extracts.

In the present invention, Phellodendri Cortex, Schizonepetae Spica, Sophorae Radix, Glycyrrhizae Radix, Liriopis Tuber, and Radix Rehmanniae Exsiccate may be purchased from commercially available sources, or collected from or grown in nature, but are not limited thereto.

The extract of the present invention may be obtained by extracting the mixture of Phellodendri Cortex, Schizonepetae Spica, Sophorae Radix, Glycyrrhizae Radix, Liriopis Tuber, and Radix Rehmanniae Exsiccate with one or more solvents selected from the group consisting of water, C1 to C4 alcohols, and mixed solvents thereof.

As used herein, the term "extract" includes a liquid extract itself and an extract of any formulation which may be prepared using the liquid extract, such as a liquid extract obtained by extracting the mixture of Phellodendri Cortex, Schizonepetae Spica, Sophorae Radix, Glycyrrhizae Radix, Liriopis Tuber, and Radix Rehmanniae Exsiccate, a diluted or concentrated liquid of the liquid extract, a dried product obtained by drying the liquid extract, and a crude purification product or a purification product of the liquid extract, or a mixture thereof, etc.

In the mixed extract of Phellodendri Cortex, Schizonepetae Spica, Sophorae Radix, Glycyrrhizae Radix, Liriopis Tuber, and Radix Rehmanniae Exsiccate of the present invention, a method of extracting the mixture may be, but is not particularly limited to, performed according to a method commonly used in the art. Non-limiting examples of the extraction method may include a hot water extraction method, a sonication extraction method, a filtration method, a reflux extraction method, etc., and these methods may be performed alone or in a combination of two or more thereof.

In the present invention, a kind of an extraction solvent used in extracting the mixture is not particularly limited, and any solvent known in the art may be used. Non-limiting examples of the extraction solvent may include water, alcohol, a mixture thereof, etc., and these solvents may be used alone or in a combination of one or more thereof. Specifically, water may be used. When alcohol is used as the solvent, C1 to C4 alcohols may be specifically used.

As used herein, the term "fraction" refers to a product obtained by a fractionation method of separating a particular component or a particular group from a mixture including various components.

In the present invention, a fractionation method of obtaining the fraction is not particularly limited, and may be performed according to a method commonly used in the art. Non-limiting examples of the fractionation method may include a solvent fractionation method performed by treating various solvents, an ultrafiltration fractionation method performed by passing through an ultrafiltration membrane having a specific molecular weight cut-off value, a chromatographic fractionation method performed by using various chromatographic systems (manufactured for separation based on size, charge, hydrophobicity, or affinity), and a combination thereof, etc. Specifically, an extract obtained by extracting the mixture of Phellodendri Cortex, Schizonepetae Spica, Sophorae Radix, Glycyrrhizae Radix, Liriopis Tuber, and Radix Rehmanniae Exsiccate of the present invention may be treated with a predetermined solvent to obtain a fraction from the extract.

In the present invention, a kind of a fractionation solvent used in obtaining the fraction is not particularly limited, and any solvent known in the art may be used. Non-limiting examples of the fractionation solvent may include polar solvents such as water, C1 to C4 alcohols, etc.; and non-polar solvents such as hexane, ethyl acetate, chloroform, dichloromethane, etc.; or mixtures thereof. These solvents may be used alone or in a combination of one or more thereof, but are not limited thereto.

Further, the extract or fraction may be used in a dry powder form after extraction, but is not limited thereto.

In the present invention, the mixture of Phellodendri Cortex, Schizonepetae Spica, Sophorae Radix, Glycyrrhizae Radix, Liriopis Tuber, and Radix Rehmanniae Exsiccate may include Phellodendri Cortex, Schizonepetae Spica, Sophorae Radix, Glycyrrhizae Radix, Liriopis Tuber, and Radix Rehmanniae Exsiccate is at a weight ratio of 0.5 to 1.5:0.5 to 1.5:0.5 to 1.5:0.5 to 1.5:0.5 to 1.5:0.5 to 1.5, specifically at a weight ratio of 0.7 to 1.3:0.7 to 1.3:0.7 to 1.3:0.7 to 1.3:0.7 to 1.3:0.7 to 1.3, and more specifically at a weight ratio of 1:1:1:1:1:1, but is not limited thereto.

As used herein, the term "atopic dermatitis" (AD) refers to a kind of autoimmune skin diseases, accompanied by skin abscess, eczema, itchiness. Although both environmental and genetic factors are known to be involved in the onset of atopic dermatitis, pathogenesis has not been clearly elucidated. In the present invention, atopic dermatitis may be used interchangeably with "AD".

As used herein, the term "preventing" means all of the actions by which atopic dermatitis is restrained or retarded by administration of the composition including the extract.

As used herein, the term "treating" means all of the actions by which symptoms of atopic dermatitis have taken a turn for the better or been modified favorably by administration of the composition including the extract.

In a specific embodiment of the present invention, it was confirmed that the mixed extract of Phellodendri Cortex, Schizonepetae Spica, Sophorae Radix, Glycyrrhizae Radix, Liriopis Tuber, and Radix Rehmanniae Exsiccate of the present invention may ameliorate, to an excellent degree, erythema/bleeding, edema, exfoliation/dryness, excoriation/erosion, and scleroderma, which are clinical symptoms of atopic dermatitis (FIG. 1); may inhibit infiltration of inflammatory cells or mast cells into the epidermis and dermis (FIG. 3); may decrease the number of white blood cells (FIG. 4); and may decrease levels of inflammatory cytokines such as IL-6, IL-10, and IL-12 as well as serum IgE (FIG. 5). These effects were confirmed to be superior to those of tacrolimus, which is a drug previously used for atopic dermatitis, indicating that the extract may be effectively used for the prevention or treatment of atopic dermatitis.

The pharmaceutical composition of the present invention may include the extract in an amount of 0.001% by weight to 80% by weight, specifically 0.001% by weight to 70% by weight, and more specifically 0.001% by weight to 60% by weight, based on the total weight of the composition, but is not limited thereto.

Further, the pharmaceutical composition may further include a pharmaceutically acceptable carrier, excipient, or diluent which is commonly used in the preparation of pharmaceutical compositions. The carrier may include a non-naturally occurring carrier. The carrier, excipient, and diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil.

Further, the pharmaceutical composition may be used after being formulated, according to a common method, into a tablet, a pill, a powder, a granule, a capsule, a suspension, a solution for internal use, an emulsion, a syrup, a sterilized aqueous solution, a non-aqueous solution, a suspension, an emulsion, a lyophilized preparation, a transdermal preparation, a gel, a lotion, an ointment, a cream, a patch, a cataplasma form, a paste, a spray, a skin emulsion, a skin suspension, a transdermal patch, a drug-containing bandage, or a suppository. Specifically, the preparation may be formulated with commonly used diluents or excipients, such as fillers, extenders, binders, wetting agents, disintegrants, surfactants, etc. Solid formulations for oral administration may include tablets, pills, powders, granules, capsules, etc., but are not limited thereto. Such solid formulations may be prepared by mixing with at least one excipient, for example, starch, calcium carbonate, sucrose, lactose, gelatin, etc. In addition to simple excipients, lubricants such as magnesium stearate or talc may also be used. Liquid formulations for oral administration may be prepared by adding various excipients, for example, wetting agents, flavoring agents, aromatics, preservatives, etc., in addition to liquid paraffin. Formulations for parenteral administration may include sterile aqueous solutions, non-aqueous solvents, suspensions, emulsions, lyophilized preparations, and suppositories. The non-aqueous solutions and the suspensions may include propylene glycol, polyethylene glycol, vegetable oil such as olive oil, injectable ester such as ethyloleate, etc. The base for suppositories may include witepsol, macrogol, tween 61, cacao butter, laurin butter, glycerogelatin, etc.

Another aspect provides a method of treating atopic dermatitis, the method including the step of administering the pharmaceutical composition to a subject suspected of having atopic dermatitis, excluding humans.

As used herein, the term "administration" means introducing the composition including the extract into a subject by any suitable method.

As used herein, the term "subject" means all animals of rats, mice, and livestock, including humans, which have developed or are at risk of developing atopic dermatitis. Specific examples thereof may be mammals including humans.

The pharmaceutical composition of the present invention may be administered in a pharmaceutically effective amount. As used herein, the term "pharmaceutically effective amount" means an amount which is sufficient to treat diseases at a reasonable benefit/risk ratio applicable to any medical treatment. The effective dosage level may be determined depending on factors including a kind of a subject and severity, age, sex, activity of a drug, drug sensitivity, administration time, administration route, excretion rate, duration of treatment, drugs used concurrently, and other factors known in the medical field. For example, the mixed extract of Phellodendri Cortex, Schizonepetae Spica, Sophorae Radix, Glycyrrhizae Radix, Liriopis Tuber, and Radix Rehmanniae Exsiccate may be administered in a daily dosage of 0.01 mg/kg to 500 mg/kg, and specifically 10 mg/kg to 100 mg/kg. The dose may be administered once per day or in several divided doses per day.

The pharmaceutical composition may be administered alone or in combination with other therapeutic agents, and may be administered sequentially or simultaneously with existing therapeutic agents. The composition may be administered in a single or multiple dosage form. It is important to administer the composition in a minimum amount that may exhibit a maximum effect without causing side effects, considering all the above-described factors. The amount may be readily determined by those skilled in the art.

Further, the pharmaceutical composition may be administered orally or parenterally (e.g., intravenous, subcutaneous, intraperitoneal or topical administration) depending on the purpose, and the administration dose may be properly selected by those skilled in the art, depending on a patient's conditions and body weight, severity of a disease, preparation of a drug, and administration route and time.

Still another aspect provides a food composition for ameliorating atopic dermatitis, the food composition including the mixed extract of Phellodendri Cortex, Schizonepetae Spica, Sophorae Radix, Glycyrrhizae Radix, Liriopis Tuber, and Radix Rehmanniae Exsiccate or a fraction thereof.

In this regard, the definitions of Phellodendri Cortex, Schizonepetae Spica, Sophorae Radix, Glycyrrhizae Radix, Liriopis Tuber, Radix Rehmanniae Exsiccate, extract, fraction, and atopic dermatitis are the same as described above.

As used herein, the term "ameliorating" means all of the actions by which parameters associated with conditions under treatment, for example, symptoms are at least lessened by administration of the composition including the extract.

As used herein, the term "food" may include meats, sausages, bread, chocolate, candies, snack, confectionery, pizza, ramen, other noodles, gums, dairy products including ice cream, various soups, beverages, teas, drinks, alcoholic beverages, multivitamin complex, health functional foods, health foods, etc., and may include all foods that are considered within conventional meaning.

Since the food composition of the present invention may be ingested routinely, high effects of ameliorating atopic dermatitis may be expected, and therefore, the food composition may be very usefully applied for the purpose of promoting health.

The term "health functional food" is the same term as food for special health use (FoSHU), and refers to a food having high medicinal and medical effects, which is processed to effectively exert a body-regulating function as well as to supply nutrients. Here, the term "functional" means that it is taken for the purpose of controlling nutrients with respect to structures and functions of the human body or of obtaining effects beneficial for health care, such as physiological effects. The food of the present invention may be prepared by a method commonly used in the art, and it may also be prepared by adding raw materials and ingredients which are generally added in the art during preparation. Further, formulations of the food may also be prepared without limitation as long as they are formulations acceptable as foods. The food composition of the present invention may be prepared in various types of formulations. Unlike general drugs, the food composition includes a natural product as a raw material, and therefore, it has advantages of being free from side effects that may occur when taken for a long period of time. The food composition is also excellent in portability, and therefore, the food of the present invention may be taken as a supplement agent for promoting the effect of ameliorating atopic dermatitis.

The health food refers to a food having an effect of actively maintaining or promoting health, compared to a general food, and a health supplement food refers to a food for health supplement. In some cases, the terms "health functional foods", "health foods", and "health supplement foods" are used interchangeably.

Specifically, the health functional food is a food prepared by adding the compound of the present invention to a food material such as beverages, teas, flavors, gums, confectionery, etc., or prepared as a capsule, powder, or suspension, and the health functional food means a food that elicits a particular effect on health when taken. Unlike general drugs, the food composition includes a food as a raw material, and therefore, it has advantages of being free from side effects that may occur when taken for a long period of time.

The food composition may further include a physiologically acceptable carrier, and the kind of the carrier is not particularly limited, and any carrier may be used as long as it is commonly used in the art.

Further, the food composition may further include an additional ingredient capable of improving smell, taste, appearance, etc. which is commonly used in the food composition. For example, the food composition may include vitamin A, C, D, E, B 1, B2, B6, or B12, niacin, biotin, folate, panthotenic acid, etc. Further, the food composition may include minerals such as zinc (Zn), iron (Fe), calcium (Ca), chromium (Cr), magnesium (Mg), manganese (Mn), copper (Cu) chromium (Cr), etc.; and amino acids such as lysine, tryptophan, cysteine, valine, etc.

Further, the food composition may include food additives such as preservatives (potassium sorbate, sodium benzoate, salicylic acid, sodium dehydroacetate, etc.), disinfectants (bleaching powder, higher bleaching powder, sodium hypochlorite, etc.), antioxidants (butylhydroxyanisole (BHA), butylhydroxytoluene (BHT), etc.), coloring agents (tar color, etc.), color-developing agents (sodium nitrate, sodium nitrite, etc.), bleaching agents (sodium sulfite), seasonings (monosodium glutamate (MSG), etc.), sweeteners (dulcin, cyclemate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

The food composition of the present invention may be used as, for example, a health drink composition, and in this case, it may include additional ingredients such as various flavors, natural carbohydrates, etc., like common drinks. The above-described natural carbohydrates may include monosaccharides such as glucose and fructose; disaccharides such as maltose and sucrose; polysaccharides such as dextrin and cyclodextrin; sugar alcohols such as xylitol, sorbitol, erythritol, etc. The sweetener may include a natural sweetener such as thaumatin and *stevia* extract; or an artificial sweetener such as saccharin and aspartame. A content of the natural carbohydrate may be generally about 0.01 g to about 0.04 g, and specifically, about 0.02 g to about 0.03 g per 100 mL of the health drink composition of the present invention.

In addition to the above ingredients, the health drink composition may include a variety of nutrients, vitamins, electrolytes, flavoring agents, coloring agents, pectic acid and salts thereof, arginic acid and salts thereof, organic acids, protective colloidal viscosifiers, pH regulators, stabilizers, preservatives, glycerin, alcohols, carbonators, etc. The health drink composition may also include natural fruit juice, fruit juice beverages, or fruit flesh for the preparation of vegetable beverages. All of these ingredients may be added singly or in any combination thereof. A mixing ratio of those ingredients does not matter, but is generally selected in the range of 0.01 parts by weight to 0.1 parts by weight per 100 parts by weight of the health drink composition of the present invention.

Still another aspect provides a quasi-drug composition for preventing or ameliorating atopic dermatitis, the quasi-drug composition including a mixed extract of Phellodendri Cortex, Schizonepetae Spica, Sophorae Radix, Glycyrrhizae Radix, Liriopis Tuber, and Radix Rehmanniae Exsiccate or a fraction thereof.

In this regard, the definitions of Phellodendri Cortex, Schizonepetae Spica, Sophorae Radix, Glycyrrhizae Radix, Liriopis Tuber, Radix Rehmanniae Exsiccate, extract, fraction, atopic dermatitis, preventing, and ameliorating are the same as described above.

As used herein, the term "quasi-drug" refers to fibers, rubber products, or similar products used for the purpose of medical care, alleviation, treatment, or prevention of diseases in humans or animals; non-appliance, non-machinery, or similar products which have insignificant influences on or do not directly act upon human bodies; preparations used for sterilization, insecticide, and purposes similar thereto in order to prevent communicable diseases, and the quasi-drug does not include products used for the purposes of diagnosis, medical care, alleviation, treatment, or prevention of diseases of humans or animals, excluding appliances, machinery, and equipment; or products, other than appliances, machinery, or equipment, used for the purpose of exerting pharmacological effects upon the structure or functions of humans or animals. The quasi-drugs may include formulations for external application and personal hygiene products.

When the mixed extract of Phellodendri Cortex, Schizonepetae Spica, Sophorae Radix, Glycyrrhizae Radix, Liriopis Tuber, and Radix Rehmanniae Exsiccate of the present invention is added to the quasi-drug composition for preventing or ameliorating atopic dermatitis, the extract may be added as it is or used in combination with other quasi-drug components. The extract may be properly used according to a common method. The mixture amount of the active ingredient may be appropriately determined depending on the purpose of the use (prevention, health, or medical care).

The quasi-drug composition may include, but is not particularly limited to, a personal hygiene product, a skin external agent, a disinfection cleaner, a shower foam, a wet tissue, a detergent soap, a hand wash, a mask, or an ointment. The skin external agent may be prepared, but is not particularly limited to, specifically, as an ointment, a lotion, a spray, a patch, a cream, a powder, a suspension, a gel agent, or a form of gel. The personal hygiene product may be, but is not particularly limited to, specifically a soap, a wet tissue, a tissue, a shampoo, a toothpaste, a hair care product, an air freshener gel, or a wash gel.

Still another aspect provides a cosmetic composition for preventing or ameliorating atopic dermatitis, the cosmetic composition including a mixed extract of Phellodendri Cortex, Schizonepetae Spica, Sophorae Radix, Glycyrrhizae Radix, Liriopis Tuber, and Radix Rehmanniae Exsiccate or a fraction thereof.

In this regard, the definitions of Phellodendri Cortex, Schizonepetae Spica, Sophorae Radix, Glycyrrhizae Radix, Liriopis Tuber, Radix Rehmanniae Exsiccate, extract, fraction, atopic dermatitis, preventing, and ameliorating are the same as described above.

The mixed extract of Phellodendri Cortex, Schizonepetae Spica, Sophorae Radix, Glycyrrhizae Radix, Liriopis Tuber, and Radix Rehmanniae Exsiccate may be included in an amount of 0.1% by weight to 20% by weight with respect to the total weight of the composition, as in the pharmaceutical composition. Specifically, the mixed extract may be included in an amount of 0.1% by weight to 5% by weight, more specifically 0.4% by weight to 0.6% by weight, and much more specifically 0.5% by weight with respect to the total weight of the composition, but is not limited thereto.

The cosmetic composition of the present invention may include components that are commercially used in a cosmetic composition, in addition to the extract, for example, one or more additives selected from the group consisting of water, a surfactant, a humectant, a lower alcohol, a chelating agent, a sterilizer, an antioxidant, a preservative, a pigment, and a perfume.

In addition, the cosmetic composition may be prepared in any suitable formulation commercially manufactured. For example, the cosmetic composition may be formulated in a solution, an emulsion, a suspension, a paste, a cream, a lotion, a gel, a powder, a spray, a surfactant-containing cleansing oil, a soap, a liquid cleanser, a bath agent, a foundation, a makeup base, an essence, a beauty wash, a foam, a pack, a skin lotion, a sunscreen cream, or sun oil, but is not limited thereto.

When the formulation of the present invention is a solution or an emulsion, as a carrier ingredient, a solvent, a solubilizer, or an emulsifier, e.g., water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester, may be used.

When the formulation of the present invention is a suspension, as a carrier ingredient, a liquid diluent, such as water, ethanol, or propylene glycol, or a suspension, such as ethoxylated isostearyl alcohol, poly-oxyethylene sorbitol ester, and polyoxyethylene sorbitan ester, microcrystalline cellulose, aluminum metahydroxide, bentonite, or tragacanth, may be used.

When the formulation of the present invention is a paste, a cream, or a gel, as a carrier ingredient, animal oil, vegetable oil, wax, paraffin, starch, tragacanth, a cellulose derivative, polyethylene glycol, silicon, bentonite, silica, talc, or zinc oxide may be used.

When the formulation of the present invention is a powder or a spray, as a carrier ingredient, lactose, talc, silica, aluminum hydroxide, calcium silicate, or polyamide powder may be used. Particularly, when the formulation of the present invention is a spray, it may additionally include propellants, such as chlorofluorohydrocarbons, propane/butane, or dimethyl ether.

When the formulation of the present invention is a surfactant-containing cleansing, as a carrier ingredient, aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkyl amido betaine, aliphatic alcohol, fatty acid glyceride, fatty acid diethanolamide, vegetable oil, a lanolin derivative, or ethoxylated glycerol fatty acid ester may be used.

In addition, components included in the cosmetic composition may be included in an amount commonly used in the skin science field.

MODE FOR INVENTION

Hereinafter, the present invention will be described in more detail with reference to Examples. However, the following Examples are for illustrative purposes only, and the invention is not intended to be limited by the following Examples.

Preparation Example 1. Preparation of KAJD

KAJD was prepared according to the good manufacturing practices (GMP) at Hanpoong Pharm. Co Ltd., (Jeonju, Korea). KAJD was a hot water extract of a mixture including Phellodendri Cortex, Schizonepetae Spica, Sophorae Radix, Glycyrrhizae Radix, Liriopis Tuber, and Radix Rehmanniae Exsiccate at a weight ratio of 1:1:1:1:1:1, and was extracted in water, and then the solvent was completely removed using a vacuum evaporator. The product was freeze-dried to prepare an extract powder. The obtained powder was used after being dissolved in drinking water. KAJD cream for an animal test was prepared at ATEC&Co (Seoul, Korea).

Example 1. Evaluation of Atopic Dermatitis-Ameliorating Effect of KAJD

To examine effects of KAJD on atopic dermatitis (AD), DNCB (2,4-dinitrochlorobenzene) was applied to the skin of a BALB/c mouse to induce AD-like symptoms. In many studies regarding atopic dermatitis, models in which atopy-like dermatitis was induced using chemical antigens such as DNCB, 2,4-dinitrofluorobenzene, 2,4,6-trinitrothlorobenzene, etc. are used (Dearman, R J. et al, Immunology, 1995, 86, 545-550).

In detail, 6-week-old BALB/c mice (20±2 g) were used, which were purchased from Orient Inc. (Seongnam, Korea). Mice were randomly divided into control groups or experimental groups (no treatment, DNCB, DNCB+tacrolimus, DNCB+KAJD), each group including five mice. All mice were raised under a pathogen-free environment with free access to sterile distilled water and solid feed. All mouse experiments were approved by the Experimental Animal Ethics Committee of Kyung Hee University (Approval Number: KHUASP (SE)-14-014).

Thereafter, experiments were conducted through a scheme as shown in FIG. 1. To induce AD-like skin lesions, the dorsal skin of the mouse was shaved, and 100 μL of 2% DNCB was applied thereto using a patch of 1 cm×1 cm twice a week. KAJD or tacrolimus, which is an existing therapeutic agent for AD, was periodically applied to the DNCB-applied skin for 2 weeks. At 28 days, all mice were sacrificed by $CO_2$ inhalation.

To examine changes in the skin of the BALB/c mouse by KAJD, clinical signs were observed once a week for 4 weeks. Severities of AD-like lesions in the dorsal skin, which are indicated by erythema/bleeding, edema, exfoliation/dryness, and excoriation/erosion, were scored according to a scale of 0 to 3 (0: absent, 1: mild, 2: moderate, 3: severe). Individual scores were added, and clinical skin scores were defined according to a scale of 0 to 12.

As a result, as shown in FIG. 2A, it was confirmed that significant skin hypersensitivity indicated by erythema/bleeding, edema, exfoliation/dryness, and excoriation/erosion was induced after application of DNCB. The severity of skin lesions was confirmed to persist even after sacrificing the mice. However, topical application of KAJD or tacrolimus was confirmed to remarkably reduce severe symptoms of the skin.

As shown in FIG. 2B, a clinical score of the KAJD-treated group was 3.13±1.27 and a clinical score of the tacrolimus-treated group was 3.29±0.76, which are much lower than a clinical score of the DNCB-treated group of 5.5±1.38.

Further, as shown in FIG. 2C, DNCB induced severe scleroderma, and this symptom was confirmed to remarkably decrease due to treatment with KAJD or tacrolimus.

Lastly, as shown in FIG. 2D, the spleen weight increased due to treatment with DNCB was also confirmed to remarkably decrease due to treatment with KAJD or tacrolimus.

These results suggest that KAJD effectively alleviates DNCB-induced AD-like symptoms, and its effects on scleroderma and spleen weight are more excellent than the existing drug, tacrolimus.

Further, as shown in FIGS. 3A and 3B, there was no difference in food intake between the DNCB-treated group and the normal control group, but the body weight of the DNCB-treated group was decreased by 15%, as compared with that of the normal control group. The KAJD or tacrolimus-treated group also showed similar patterns to the DNCB-treated group.

Example 2. Confirmation of Inhibitory Effects of KAJD on Infiltration of Inflammatory Cells and Mast Cells Skin infiltration of inflammatory cells or mast cells induces allergic reactions and inflammation, leading to skin hypersensitivity. Therefore, in order to examine inhibitory effects of KAJD on infiltration of inflammatory cells and mast cells, H&E (hematoxylin and eosin) staining and T.B. (toluidine blue) staining were performed.

In detail, part of a skin biopsy was fixed in 4% paraformaldehyde (PFA), and frozen sections were prepared using a frozen section compound (FSC22 Clear, Surgipath, Leica Biosystem, The Netherlands) in dry ice. To detect inflammatory cells, hematoxylin and eosin (H&E) staining was performed, and to detect mast cells, toluidine blue (T.B.) staining was performed. The stained tissues were observed under an optical microscope at 400× magnification to examine infiltration of inflammatory cells and increase or decrease of the number of mast cells.

As a result, as shown in FIGS. 4A and 4C, DNCB was confirmed to induce infiltration of inflammatory cells into both the epidermis and dermis, and KAJD treatment was confirmed to inhibit infiltration of inflammatory cells, thereby decreasing the number thereof.

Further, as shown in FIGS. 4B and 4D, DNCB was confirmed to induce infiltration of mast cells into both the epidermis and dermis, and KAJD treatment was confirmed to decrease the number of infiltrated mast cells. Further-more, inhibitory effects of KAJD on infiltration of mast cells were confirmed to be more excellent than those of tacrolimus.

Example 3. Confirmation of Reduction Effect of KAJD on Number of White Blood Cells High levels of white blood cells (WBCs) are observed in most atopic dermatitis patients. Therefore, to examine therapeutic effects of KAJD on atopic dermatitis, the number of WBCs in the blood of mice was analyzed after treatment with KAJD.

In detail, whole blood samples were collected from the heart of a mouse, and stored in a Vacutainer™ tube containing EDTA (BD Science, NJ, USA). The number of WBCs, lymphocytes, monocytes, eosinophils, basophils, or neutrophils was analyzed using a HEMAVET 950 hematology analyzer (Drew Scientific, Inc., Oxford, USA).

As a result, as shown in FIG. 5, DNCB-treated mice were confirmed to show a 3.5-fold increase in the number of WBCs, as compared with a normal control group. However, KAJD or tacrolimus was confirmed to considerably decrease the number of white blood cells which was increased by DNCB. The reduction effect of KAJD on the number of white blood cells was more excellent than that of tacrolimus. Further, KAJD and tacrolimus were confirmed to decrease the number of WBC subtypes including lymphocytes, monocytes, eosinophils, basophils, and neutrophils in similar levels to the number of WBCs. Particularly, among the cells, KAJD was confirmed to significantly decrease the number of eosinophils, which induce AD severity.

Example 4. Confirmation of Reduction Effect of KAJD on IgE and Inflammatory Cytokines Example 4-1. In Vivo Hemanalysis One of the features of AD is high expression levels of blood IgE and inflammatory cytokines. Therefore, to analyze a mechanism of anti-inflammatory activity of KAJD, levels of blood IgE and inflammatory cytokines in DNCB-treated mice were analyzed.

In detail, expression levels were analyzed by sandwich ELISA using a BD PharMingen mouse or human ELISA set (Pharmingen, San Diego, Calif., USA). A plate was coated with a capture antibody contained in an ELISA coating buffer (Sigma, St. Louis, Mo., USA), and stored at 4° C. for one day. The plate was washed with 0.05% PBS-Tween 20, and subsequently, blocked with 10% FBS-containing PBS at 20° C. for 1 hour. A standard antigen or sample serially diluted with a dilution buffer (10% FBS-containing PBS) was put in the plate, followed by incubation at 20° C. for 1 hour. Thereafter, biotin-conjugated anti-mouse IgE and SAv-HRP (streptavidin-horseradish peroxidase conjugate) was added to the plate, followed by incubation at 20° C. for 1 hour. Lastly, a TMB (tetramethylbenzidine) substrate solution was added to the plate, and incubated under dark conditions for 15 minutes, and then the reaction was terminated with a 2 N $H_2SO_4$ solution. Optical density was measured using an ELISA reader (Versa Max, Molecular Devices, CA, USA) at 450 nm.

As a result, as shown in FIG. 6, DNCB-treated mice showed increased levels of inflammatory cytokines including IL-6, IL-10, and IL-12, and in particular, high levels of IgE. However, KAJD and tacrolimus were confirmed to considerably inhibit production of serum IgE and inflammatory cytokines. Further, KAJD was confirmed to more effectively decrease the DNCB-induced IgE and IL-6 levels than tacrolimus. These results suggest that KAJD decreases concentrations of serum IgE and proinflammatory cytokines which were increased by DNCB, thereby inhibiting skin inflammation.

Example 4-2. In Vitro Analysis

Example 4-2-1. Analysis of Protein Expression Level

To analyze a mechanism of anti-inflammatory activity of KAJD, KAJD activity was evaluated at a cell level, and protein expression levels of proinflammatory cytokines expressed by RAW 264.7 mouse macrophages and human mast cells (HMC-1) or splenocytes were analyzed.

In detail, the RAW 264.7 and HMC-1 cell lines were purchased from the Korean Cell Line Bank (Seoul, Korea). Each cell line was cultured in a medium containing 10% FBS (Welgene, Daegu, Korea) and 1% antibiotic (Ab, Welgene, Daegu, Korea), and cultured in Dulbecco's modified Eagle's medium (DMEM, Welgene, Daegu, Korea) or Iscove's Modified Dulbecco's Medium (IMDM, Welgene, Daegu, Korea) in an incubator at 5% $CO_2$ and 37° C.

Further, the spleen was homogenized in RPMI-1640 medium (containing 10% FBS, 1% Ab, and 0.05 mM mercaptoethanol) under aseptic conditions. Red blood cells were eliminated using a red blood cell lysis buffer (Sigma, St. Louis, Mo., USA). The suspension was centrifuged, and then a pellet was resuspended in RPMI-1640, and separated splenocytes were incubated in an incubator at 5% $CO_2$ and 37° C.

Thereafter, the level of each cytokine was measured by ELISA described in Example 4-1, and NO production was measured using a Griess reagent kit (Promega, Madison, Wis., USA). 150 μL of RAW 264.7 cell supernatant was mixed with 150 μL of Griess reagent. This mixture was transferred to a 96-well plate and incubated at room temperature for 30 minutes. Optical density was measured using an ELISA reader (Versa Max, Molecular Devices, CA, USA) at 570 nm.

As a result, as shown in FIG. 7, expressions of cytokines of IL-6, IL-10, and TNF-α, and NO production were confirmed to be remarkably increased in LPS (lipopolysaccharide)-stimulated RAW264.7 cells. However, KAJD treatment was confirmed to remarkably decrease the cytokine expression and to decrease NO production in a concentration-dependent manner.

Further, as shown in FIG. 8, IL-6 levels were increased in splenocytes or HMC-1 cells which were activated in an inflammatory state, but KAJD treatment remarkably decreased the cytokine expression.

Example 4-2-2. Analysis of mRNA Expression Level

Example 4-2-1 confirmed that KAJD decreases protein expression levels of proinflammatory cytokines. Therefore, to examine whether KAJD regulates the cytokine expression at a transcriptional level, mRNA expression levels were analyzed.

In detail, the cells of Example 4-2-1 were obtained by centrifugation, and then, from the pellet, RNA was extracted using an easy-blue RNA extraction kit (iNtRON Biotech, Korea). The quantity of the extracted RNA was measured using a NanoDrop ND-1000 spectrophotometer (NanoDrop Technologies Inc., Wilmington, Del., USA). 2 μg of total RNA separated from each sample was reverse-transcribed using a cDNA synthesis kit (TaKaRa, Otsu, Shinga, Japan). Thereafter, 20 μL of a PCR reaction mixture was prepared by mixing a DNA template, 10 pM of each gene-specific primer, 10×Taq buffer, a 2.5 mM dNTP mixture, and 1 unit of Taq DNA polymerase (Takara, Otsu, Shinga, Japan). Sequences of respective primers are summarized in Table 1 below.

TABLE 1

| Primer type | Primer name | Section | Primer sequence |
|---|---|---|---|
| Mouse | IL-4 | SEQ ID NO: 1 | F: 5'-TCG GCA TTT TGA ACG AGG TC-3' |
| | | SEQ ID NO: 2 | R: 5'-GAA AAG CCC GAA AGA GTC TC-3' |
| | IL-6 | SEQ ID NO: 3 | F: 5'-CAA GAG ACT TCC ATC CAG TTG C-3' |
| | | SEQ ID NO: 4 | R: 5'-TTG CCG AGT TCT CAA AGT GAC-3' |
| | COX-2 | SEQ ID NO: 5 | F: 5'-AAG ACT TGC CAG GCT GAA CT-3' |
| | | SEQ ID NO: 6 | R: 5'-CTT CTG CAG TCC CAG GTT CAA-3' |
| | iNOS | SEQ ID NO: 7 | F: 5'-AAT GGC AAC ATC AGG TCG GCC ATC ACT-3' |
| | | SEQ ID NO: 8 | R: 5'-GCT GTG TGT CAC AGA AGT CTC GAA CTC-3' |
| | TNF-α | SEQ ID NO: 9 | F: 5'-ATG AGC ACA GAA AGC ATG ATC-3' |
| | | SEQ ID NO: 10 | R: 5'-TAC AGG CTT GTC ACT GGA ATT-3' |
| | GAPDH | SEQ ID NO: 11 | F: 5'-GAG GGG CCA TCC ACA GTC TTC-3' |
| | | SEQ ID NO: 12 | R: 5'-CAT CAC CAT CTT CCA GGA GCG-3' |
| Human | IL-4 | SEQ ID NO: 13 | F: 5'-TGC CTC CAA GAA CAC AAC TG-3' |
| | | SEQ ID NO: 14 | R: 5'-CTC TGG TTG GCT TCC TTC AC-3' |
| | IL-6 | SEQ ID NO: 15 | F: 5'-AAC CTT CCA AAG ATG GCT AGG-3' |
| | | SEQ ID NO: 16 | R: 5'-CAG GAA CTG GAT CAG GAC TTT-3' |
| | IL-13 | SEQ ID NO: 17 | R: 5'-GGT CAA CAT CAC CCA GAA CC-3' |
| | | SEQ ID NO: 18 | R: 5'-TTT ACA AAC TGG GCC ACC TC-3' |
| | GAPDH | SEQ ID NO: 19 | F: 5'-CGT CTT CAC CAC CAT GGA GA-3' |
| | | SEQ ID NO: 20 | R: 5'-CGG CCA TCA CGC CAC AGT TT-3' |

As a result, as shown in FIG. 9, increased IL-4 and IL-6 mRNA levels in splenocytes (FIG. 9A) and HMC-1 cells (FIG. 9B) were confirmed to decrease by KAJD treatment. In particular, when KAJD was treated at a concentration of 500 μg/mL, both IL-4 and IL-6 levels were decreased, as compared with those of a control group.

These results suggest that KAJD regulates production of proinflammatory cytokines by immune cells, thereby decreasing DNCB-induced AD-like symptoms.

Example 5. Confirmation of Reduction Effect of KAJD on Viability of Inflammatory Cells To examine anti-inflammatory activity of KAJD, viability of RAW 264.7 or splenocytes was analyzed.

In detail, each of the cells was dispensed at a density of 1×10$^4$ cells/well in a 96-well plate, and cultured for 24 hours. Thereafter, in the presence or absence of various concentrations of KAJD, RAW 264.7 and splenocytes were treated with 1 μg/mL of LPS to activate cells in an inflammatory state. After incubation for 24 hours, 10 μL of WST solution was added to each well, and the plate was incubated under dark conditions for an additional 1 hour. Thereafter, an ELISA reader (Versa Max, Molecular Devices, CA, USA) was used to measure optical density at 450 nm.

As a result, as shown in FIG. 10A, viability of LPS-treated RAW 264.7 cells was increased by about 1.5 times, as compared with that of a control group. KAJD treatment was confirmed to decrease the increased viability of the LPS-treated cells in a concentration-dependent manner.

Further, as shown in FIG. 10B, viability of LPS-treated splenocytes was increased, as compared with that of a control group. KAJD treatment of a high concentration of 1000 μg/mL or more was confirmed to decrease the increased viability of the LPS-treated cells in a concentration-dependent manner.

Meanwhile, as shown in FIG. 10C, the number of HMC-1 cells was not increased, although the cells were treated with PMA and ionomycin, which are inflammatory stimulants. This result is consistent with the previous study reporting that no significant change in the number of HMC-1 cells is caused even though the cells are activated in an inflammatory state.

Example 6. Comparison of Inflammation-Reducing Effects Between Mixed Herbal Medicine Extract (KAJD) and Single Herbal Medicine Extracts Example 6-1. Comparison of Inflammatory Cell Viability-Reducing Effects To examine anti-inflammatory effects of KAJD, its effect of reducing viability of HMC-1 mast cells which are activated in an inflammatory state was compared with those of individual herbal medicine extracts constituting KAJD.

In detail, HMC-1 mast cells were treated with a single extract of Phellodendri Cortex, Liriopis Tuber, Schizonepetae Spica, Radix Rehmanniae Exsiccate, Sophorae Radix, or Glycyrrhizae Radix, or KAJD, and then treated with 5 ng/mL PMA and 500 ng/mL ionomycin to activate the cells in an inflammatory state. After incubation for 24 hours, viability of HMC-1 was examined by MTT assay.

As a result, as shown in FIGS. 11A, 11B, and 12, the single extract of Phellodendri Cortex, Liriopis Tuber, Schizonepetae Spica, Radix Rehmanniae Exsiccate, or Glycyrrhizae Radix, excluding Sophorae Radix, did not affect the number of activated HMC-1 cells, whereas KAJD significantly decreased the number of activated HMC-1 cells, as compared with a control group.

Example 6-2. Comparison of Reduction Effects on Proinflammatory Cytokine Expression Levels of Inflammatory Cells To examine anti-inflammatory effects of KAJD, its effect of reducing expression levels of proinflammatory cytokines was compared with those of individual herbal medicine extracts constituting KAJD.

In detail, HMC-1 cells were treated with a single extract of Phellodendri Cortex, Liriopis Tuber, Schizonepetae Spica, Radix Rehmanniae Exsiccate, Sophorae Radix, or Glycyrrhizae Radix, or KAJD, and then treated with 5 ng/mL PMA and 500 ng/mL ionomycin to activate the cells in an inflammatory state. After incubation for 24 hours, PCR was performed according to the method of Example 4-2-2.

As a result, as shown in FIG. 13, KAJD was confirmed to remarkably decrease mRNA expression levels of IL-4, IL-6, IL-13, and TNF-α, which are proinflammatory cytokines, as compared with the single extract of Phellodendri Cortex, Liriopis Tuber, Schizonepetae Spica, Radix Rehmanniae Exsiccate, Sophorae Radix, or Glycyrrhizae Radix.

These results suggest that the mixed herbal medicine extract of the present invention may decrease inflammation to a degree superior to the single extract of Phellodendri Cortex, Liriopis Tuber, Schizonepetae Spica, Radix Rehmanniae Exsiccate, Sophorae Radix, or Glycyrrhizae Radix.

Example 7. Comparison of Inflammation-Reducing Effects According to Mixing Ratio of KAJD Example 7-1. Comparison of Inflammatory Cell Viability-Reducing Effects To examine a mixing ratio of Phellodendri Cortex, Liriopis Tuber, Schizonepetae Spica, Radix Rehmanniae Exsiccate, Sophorae Radix, and Glycyrrhizae Radix, which exhibits the most excellent anti-inflammatory activity, the following experiment was performed.

In detail, a mixed herbal medicine extract (D1 or D2) including Phellodendri Cortex, Liriopis Tuber, Schizonepetae Spica, Radix Rehmanniae Exsiccate, Sophorae Radix, and Glycyrrhizae Radix at a weight ratio of 1:1:1:1:2:1 or 1:1:1:1:1:2 was additionally prepared. Thereafter, in the presence or absence of 500 μg/mL of the mixed herbal medicine extract, HMC-1 cells were activated in an inflammatory state by treatment with 5 ng/mL PMA and 500 ng/mL ionomycin. After incubation for 24 hours, viability of HMC-1 mast cells was examined by MTT assay.

As a result, as shown in FIG. 14, the mixed herbal medicine extract (D1 or D2) including Phellodendri Cortex, Liriopis Tuber, Schizonepetae Spica, Radix Rehmanniae Exsiccate, Sophorae Radix, and Glycyrrhizae Radix at a weight ratio of 1:1:1:1:2:1 or 1:1:1:1:1:2 did not affect the number of activated HMC-1 cells, whereas the mixed herbal medicine extract (KAJD; D) including the herbal medicines at a weight ratio of 1:1:1:1:1:1 significantly decreased the number of activated HMC-1 cells, as compared with a control group.

Example 7-2. Comparison of Reduction Effects on Proinflammatory Cytokine Expression Levels of Inflammatory Cells To examine a mixing ratio of Phellodendri Cortex, Liriopis Tuber, Schizonepetae Spica, Radix Rehmanniae Exsiccate, Sophorae Radix, and Glycyrrhizae Radix, which exhibits the most excellent anti-inflammatory activity, the mixed herbal medicine extract (D1 or D2) including Phellodendri Cortex, Liriopis Tuber, Schizonepetae Spica, Radix Rehmanniae Exsiccate, Sophorae Radix, and Glycyrrhizae Radix at a weight ratio of 1:1:1:1:2:1 or 1:1:1:1:1:2 was prepared in the same manner as in Example 7-1, and then treated to HMC-1 cells. Thereafter, the cells were activated in an inflammatory state, and then PCR was performed in the same manner as in Example 4-2-2.

As a result, as shown in FIG. 15, the mixed herbal medicine extract (KAJD; D) including Phellodendri Cortex, Liriopis Tuber, Schizonepetae Spica, Radix Rehmanniae Exsiccate, Sophorae Radix, and Glycyrrhizae Radix at a weight ratio of 1:1:1:1:1:1 was confirmed to remarkably decrease mRNA expression levels of IL-4, IL-6, IL-13, and TNF-α, which are proinflammatory cytokines, as compared with the mixed herbal medicine extract (D1 or D2) including the herbal medicines at a weight ratio of 1:1:1:1:2:1 or 1:1:1:1:1:2.

These results suggest that when the mixed herbal medicine extract of the present invention includes Phellodendri Cortex, Liriopis Tuber, Schizonepetae Spica, Radix Rehmanniae Exsiccate, Sophorae Radix, and Glycyrrhizae Radix at a weight ratio of 1:1:1:1:1:1, it may exhibit excellent inflammation-reducing effects.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the present invention is defined by the appended claims rather than by the description preceding them, and therefore all changes and modifications that fall within metes and bounds of the claims, or equivalents of such metes and bounds, are therefore intended to be embraced by the claims.

The invention claimed is:

1. A pharmaceutical composition for preventing or treating atopic dermatitis, the pharmaceutical composition comprising a mixed extract consisting of Phellodendri Cortex, Schizonepetae Spica, Sophorae Radix, Glycyrrhizae Radix, Liriopis Tuber, and Radix Rehmanniae Exsiccate or a fraction thereof as an active ingredient, wherein the mixed extract is a hot water extract obtained by extracting a mixture of Phellodendri Cortex, Schizonepetae Spica, Sophorae Radix, Glycyrrhizae Radix, Liriopis Tuber, and Radix Rehmanniae Exsiccate at a weight ratio of 1:1:1:1:1:1.

2. The pharmaceutical composition of claim 1, wherein the composition includes the mixed extract of Phellodendri Cortex, Schizonepetae Spica, Sophorae Radix, Glycyrrhizae Radix, Liriopis Tuber, and Radix Rehmanniae Exsiccate in an amount of 0.001% by weight to 80% by weight with respect to the total weight of the composition.

3. The pharmaceutical composition of claim 1, further comprising a pharmaceutically acceptable carrier, excipient, or diluent.

4. The pharmaceutical composition of claim 1, wherein the composition has any one formulation selected from the group consisting of a tablet, a pill, a powder, a granule, a capsule, a suspension, a solution for internal use, an emulsion, a syrup, a sterilized aqueous solution, a non-aqueous solution, a lyophilized preparation, a transdermal preparation, a gel, a lotion, an ointment, a cream, a patch, a cataplasma form, a paste, a spray, a drug-containing bandage, and a suppository.

5. A method of treating atopic dermatitis, the method comprising the step of administering a pharmaceutical composition for treating atopic dermatitis to a subject suspected of having atopic dermatitis, excluding humans, wherein the pharmaceutical composition contains a mixed extract of Phellodendri Cortex, Schizonepetae Spica, Sophorae Radix, Glycyrrhizae Radix, Liriopis Tuber, and Radix Rehmanniae Exsiccate, or a fraction thereof wherein the mixed extract is a hot water extract obtained by extracting a mixture of Phellodendri Cortex, Schizonepetae Spica, Sophorae Radix, Glycyrrhizae Radix, Liriopis Tuber, and Radix Rehmanniae Exsiccate at a weight ratio of 1:1:1:1:1:1.

6. A food composition for ameliorating atopic dermatitis, the food composition comprising a mixed extract of Phellodendri Cortex, Schizonepetae Spica, Sophorae Radix, Glycyrrhizae Radix, Liriopis Tuber, and Radix Rehmanniae Exsiccate or a fraction thereof as an active ingredient, wherein the mixed extract is a hot water extract obtained by extracting a mixture of Phellodendri Cortex, Schizonepetae Spica, Sophorae Radix, Glycyrrhizae Radix, Liriopis Tuber, and Radix Rehmanniae Exsiccate at a weight ratio of 1:1:1:1:1:1.

7. A quasi-drug composition for preventing or ameliorating atopic dermatitis, the quasi-drug composition comprising a mixed extract consisting of Phellodendri Cortex, Schizonepetae Spica, Sophorae Radix, Glycyrrhizae Radix, Liriopis Tuber, and Radix Rehmanniae Exsiccate or a fraction thereof as an active ingredient, wherein the mixed extract is a hot water extract obtained by extracting a mixture of Phellodendri Cortex, Schizonepetae Spica, Sophorae Radix, Glycyrrhizae Radix, Liriopis Tuber, and Radix Rehmanniae Exsiccate at a weight ratio of 1:1:1:1:1:1.

8. A cosmetic composition for ameliorating atopic dermatitis, the cosmetic composition comprising a mixed extract consisting of Phellodendri Cortex, Schizonepetae Spica, Sophorae Radix, Glycyrrhizae Radix, Liriopis Tuber, and Radix Rehmanniae Exsiccate or a fraction thereof as an active ingredient, wherein the mixed extract is a hot water extract obtained by extracting a mixture of Phellodendri Cortex, Schizonepetae Spica, Sophorae Radix, Glycyrrhizae Radix, Liriopis Tuber, and Radix Rehmanniae Exsiccate at a weight ratio of 1:1:1:1:1:1.

9. The method of claim 5, wherein the composition includes the mixed extract of Phellodendri Cortex, Schizonepetae Spica, Sophorae Radix, Glycyrrhizae Radix, Liriopis Tuber, and Radix Rehmanniae Exsiccate in an amount of 0.001% by weight to 80% by weight with respect to the total weight of the composition.

10. The method of claim 5, wherein the composition further contains a pharmaceutically acceptable carrier, excipient, or diluent.

11. The method of claim 5, wherein the composition has any one formulation selected from the group consisting of a tablet, a pill, a powder, a granule, a capsule, a suspension, a solution for internal use, an emulsion, a syrup, a sterilized aqueous solution, a non-aqueous solution, a lyophilized preparation, a transdermal preparation, a gel, a lotion, an ointment, a cream, a patch, a cataplasma form, a paste, a spray, a drug-containing bandage, and a suppository.

* * * * *